(12) United States Patent
Lim et al.

(10) Patent No.: US 8,628,939 B2
(45) Date of Patent: Jan. 14, 2014

(54) EXPRESSION VECTOR CONTAINING THE MAJOR ENVELOPE PROTEIN P9 OF CYSTOVIRUS PHI6 AS A FUSION PARTNER, AND PROCESS FOR PRODUCING A MEMBRANE PROTEIN USING THE SAME

(75) Inventors: Dong-bin Lim, Seoul (KR); Yuna Jung, Seoul (KR)

(73) Assignee: Foundation of Soongsil University—Industry Cooperation, Seoul (KR)

( * ) Notice: Subject to any disclaimer, the term of this patent is extended or adjusted under 35 U.S.C. 154(b) by 103 days.

(21) Appl. No.: 13/058,425

(22) PCT Filed: Aug. 13, 2009

(86) PCT No.: PCT/KR2009/004525
§ 371 (c)(1),
(2), (4) Date: Aug. 4, 2011

(87) PCT Pub. No.: WO2010/019006
PCT Pub. Date: Feb. 18, 2010

(65) Prior Publication Data
US 2011/0287484 A1    Nov. 24, 2011

(30) Foreign Application Priority Data

Aug. 13, 2008  (KR) .................. 10-2008-0079542

(51) Int. Cl.
*C12P 21/00* (2006.01)
*C12N 9/00* (2006.01)
*C12N 5/10* (2006.01)
*C12N 1/00* (2006.01)
*C12N 15/63* (2006.01)

(52) U.S. Cl.
USPC .................... 435/69.6; 435/252.33; 435/183; 435/243; 435/69.1; 435/320.1

(58) Field of Classification Search
None
See application file for complete search history.

(56) References Cited

PUBLICATIONS

White, J. F., et al. Automated Large Scale purification of a G-protein-coupled receptor for neurotensin FEBS Lett. 564:289, 2004.*

* cited by examiner

*Primary Examiner* — Kagnew H Gebreyesus
(74) *Attorney, Agent, or Firm* — Nath, Goldberg & Meyer; Joshua B. Goldberg; Tanya E. Harkins

(57) ABSTRACT

The present invention relates to a membrane protein expression vector containing the major envelope protein P9 of Cystovirus phi6 as a fusion partner, to cells transformed by the expression vector, and to a process for producing membrane proteins using the cells. Target proteins can be effectively expressed by the expression vector of the present invention.

17 Claims, 13 Drawing Sheets

Figure 1

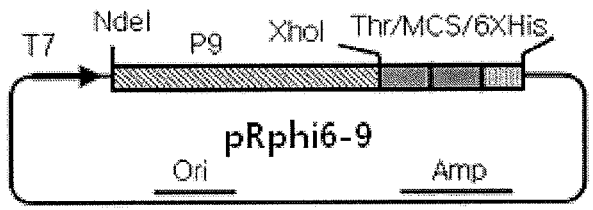

Figure 2

SEQ ID NO. 5

```
                                                pRSET  ←——:——→ P9
                                                            M  P  F  P  L  V  K  Q  D  P  T
  1  TCCCTCTAGAAATAATTTTGTTTAACTTTAAGAAGGAGATATACATATGCCGTTTCCGCTGGTGAAACAGGACCCGACCA  80
  1  AGGGAGATCTTTATTAAAACAAATTGAAATTCTTCCTCTATATGTATACGGCAAAGGCGACCACTTTGTCCTGGGCTGGT  80
                                                 Ndel S  K  A  F  T  E  A  S  E  R  S  T  G  T  Q  I  L  D  V  V  K  A  P  I  G  L  F
 81  GCAAAGCGTTCACCGAAGCCAGCGAACGCTCCACCGGCACCCAGATCCTGGACGTCGTGAAGGCCCCGATCGGCCTGTTC  160
 81  CGTTTCGCAAGTGGCTTCGGTCGCTTGCGAGGTGGCCGTGGGTCTAGGACCTGCAGCACTTCCGGGGCTAGCCGGACAAG  160

G  D  D  A  K  H  E  F  V  T  R  Q  E  Q  A  V  S  V  V  S  W  A  V  A  A  G  L
161  GGCGACGATGCCAAACACGAGTTCGTGACCCGTCAGGAACAAGCGGTCAGCGTTGTCAGCTGGGCGGTTGCGGCCGGTCT  240
161  CCGCTGCTACGGTTTGTGCTCAAGCACTGGGCAGTCCTTGTTCGCCAGTCGCAACAGTCGACCCGCCAACGCCGGCCAGA  240

End of P9 ——→:
        I  C  E  L  I  G  Y  R  G  A  R  S  G  R  K  A  I  L  A  N  I  P  F  L  A  I
241  GATCTGCGAGCTGATCGGCTACCGTGGTGCGCGCTCGGGTCGCAAAGCGATCCTGGCCAACATTCCGTTTCTGGCGATCT  320
241  CTAGACGCTCGACTAGCCGATGGCACCACGCGCGAGCCCAGCGTTTCGCTAGGACCGGTTGTAAGGCAAAGACCGCTAGA  320
                                                                                    Xhol

* * * */ * * ←—— Thr recognition site
        S  S  L  V  P  R  G  S  R  A  A  A  G  T  M  E  A  S  H  H  H  H  H  H  *
321  CGAGCCTGGTGCCGCGCGGCTCCCGGGCTGCAGCTGGTACCATGGAAGCTTCTCACCATCACCATCACCATTAACTTAAG  400
321  GCTCGGACCACGGCGCGCCGAGGGCCCGACGTCGACCATGGTACCTTCGAAGAGTGGTAGTGGTAGTGGTAATTGAATTC  400
                    Smal Pst PvuII KpnI NcoI HindIII                        AflII :——→ pRSET
401  TCCGGAGCTTGATCCGGCTGCTAACAAAGCCCGAAAGGAAGCTGAGTTGGCTGCTGCCACCGCTGAGCAATAACTAGCAT  480
401  AGGCCTCGAACTAGGCCGACGATTGTTTCGGGCTTTCCTTCGACTCAACCGACGACGGTGGCGACTCGTTATTGATCGTA  480
```

Figure 12

SEQ ID NO: 36

```
     M  P  F  P  L  V  K  Q  D  P  T  S  K  A  F  T  E  A  S  E  R  S  T  G  T  Q  I
1    ATGCCGTTTCCGCTGGTGAAACAGGACCCGACCAGCAAAGCGTTCACCGAAGCCAGCGAACGCTCCACCGGCACCCAGAT  80
1    TACGGCAAAGGCGACCACTTTGTCCTGGGCTGGTCGTTTCGCAAGTGGCTTCGGTCGCTTGCGAGGTGGCCGTGGGTCTA  80
                                                                              TM domain
     L  D  V  V  K  A  P  I  G  L  F  G  D  D  A  K  H  E  F  V  T  R  Q  E  Q  A
81   CCTGGACGTCGTGAAGGCCCCGATCGGCCTGTTCGGCGACGATGCCAAACACGAGTTCGTGACCCGTCAGGAACAAGCGG  160
81   GGACCTGCAGCACTTCCGGGGCTAGCCGGACAAGCCGCTGCTACGGTTTGTGCTCAAGCACTGGGCAGTCCTTGTTCGCC  160

V  S  V  V  S  V  A  V  A  A  G  L  I  C  E  L  I  G  Y  R  G  A  R  S  G  R  K
161  TCAGCGTTGTCAGCTGGGCGGTTGCGGCCGGTCTGATCTGCGAGCTGATCGGCTACCGTGGTGCGCGCTCGGGTCGCAAA  240
161  AGTCGCAACAGTCGACCCGCCAACGCCGGCCAGACTAGACGCTCGACTAGCCGATGGCACCACGCGCGAGCCCAGCGTTT  240
                                                                     Fragment containing TM
     A  I  L  A  N  I  S  T  R  Q  E  Q  A  V  S  V  V  S  V  A  V  A  A  G  L  I  G
241  GCGATCCTGGCCAACATT TCGACCCGCCAAGAGCAGGCCGTTTCGGTTGTGTCATGGGCCGTGGCAGCAGGTCTGATTGG  320
241  CGCTAGGACCGGTTGTAA AGCTGGGCGGTTCTCGTCCGGCAAAGCCAACACAGTACCCGGCACCGTCGTCCAGACTAACC  320

E  L  I  G  Y  R  G  A  R  S  G  R  K  A  I  L  A  N  I  P  F  L  A  I  S  S
321  TGAACTGATTGGTTATCGCGGCGCACGTTCGGGTCGCAAAGCGATCCTGGCCAACATT CCGTTTCTGGCGATCTCGAGCC  400
321  ACTTGACTAACCAATAGCGCCGCGTGCAAGCCCAGCGTTTCGCTAGGACCGGTTGTAA GGCAAAGACCGCTAGAGCTCGG  400
                                                                                    XhoI

*  *  *  */  *  *  Thr recognition site
     L  V  P  R  G  S  R  A  A  A  G  T  M  E  A  S  H  H  H  H  H  H  *
401  TGGTGCCGCGCGGCTCCCGGGCTGCAGCTGGTACCATGGAAGCTTCTCACCATCACCATCACCATTAACTTAAG  474
401  ACCACGGCGCGCCGAGGGCCCGACGTCGACCATGGTACCTTCGAAGAGTGGTAGTGGTAGTGGTAATTGAATTC  474
         SmaI  PstI  PvuII  KpnI  NcoI  HindIII                           AflII
```

Figure 13

SEQ ID NO: 38

```
      M  P  F  P  L  V  K  Q  D  P  T  S  K  A  F  T  E  A  S  E  R  S  T  G  T  Q  I
  1 ATGCCGTTTCCGCTGGTGAAACAGGACCCGACCAGCAAAGCGTTCACCGAAGCCAGCGAACGCTCCACCGGCACCCAGAT 80
  1 TACGGCAAAGGCGACCACTTTGTCCTGGGCTGGTCGTTTCGCAAGTGGCTTCGGTCGCTTGCGAGGTGGCCGTGGGTCTA 80

L  D  V  V  K  A  P  I  G  L  F  G  D  D  A  K  H  E  F  V  T  R  Q  E  Q  A
 81 CCTGGACGTCGTGAAGGCCCCGATCGGCCTGTTCGGCGACGATGCCAAACACGAGTTCGTGACCCGTCAGGAACAAGCGG 160
 81 GGACCTGCAGCACTTCCGGGGCTAGCCGGACAAGCCGCTGCTACGGTTTGTGCTCAAGCACTGGGCAGTCCTTGTTCGCC 160

V  S  V  V  S  V  A  V  A  A  G  L  I  C  E  L  I  G  Y  R  G  A  R  S  G  R  K
161 TCAGCGTTGTCAGCTGGGCGGTTGCGGCCGGTCTGATCTGCGAGCTGATCGGCTACCGTGGTGCGCGCTCGGGTCGCAAA 240
161 AGTCGCAACAGTCGACCCGCCAACGCCGGCCAGACTAGACGCTCGACTAGCCGATGGCACCACGCGCGAGCCCAGCGTTT 240

A  S  T  R  Q  E  Q  A  V  S  V  V  S  V  A  V  A  A  G  L  I  G  E  L  I  G  Y
241 GCC TCGACCCGCCAAGAGCAGGCCGTTTCCGTTGTGTCATGGGCCGTGGCAGCAGGTCTGATTGGTGAACTGATTGGTTA 320
241 CGG AGCTGGGCGGTTCTCGTCCGGCAAAGCCAACACAGTACCCGGCACCGTCGTCCAGACTAACCACTTGACTAACCAAT 320
                                                                          *  *  *  */ *
      R  G  A  R  S  G  R  K  A  I  L  A  N  I  P  F  L  A  I  S  S  L  V  P  R  G
321 TCGCGGCGCACGTTCGGGTCGCAAAGCGATCCTGGCCAACATT CCGTTTCTGGCGATCTCGAGCCTGGTGCCGCGCGGCT 400
321 AGCGCCGCGTGCAAGCCCAGCGTTTCGCTAGGACCGGTTGTAA GGCAAAGACCGCTAGAGCTCGGACCACGGCGCGCCGA 400
                                                                              XhoI
```

\* Thr recognition site
```
      S  R  A  A  A  G  T  M  E  A  S  H  H  H  H  H  H  *
401 CCCGGGCTGCAGCTGGTACCATGGAAGCTTCTCACCATCACCATCACCATTAACTTAAG 459
401 GGGCCCGACGTCGACCATGGTACCTTCGAAGAGTGGTAGTGGTAGTGGTAATTGAATTC 459
    SmaI Pst PvuII KpnI NcoI HindIII                    AflII
```

Figure 14

SEQ ID NO: 40

```
          M  P  F  P  L  V  K  Q  D  P  T  S  K  A  F  T  E  A  S  E  R  S  T  G  T  Q  I
  1  ATGCCGTTTCCGCTGGTGAAACAGGACCCGACCAGCAAAGCGTTCACCGAAGCCAGCGAACGCTCCACCGGCACCCAGAT   80
  1  TACGGCAAAGGCGACCACTTTGTCCTGGGCTGGTCGTTTCGCAAGTGGCTTCGGTCGCTTGCGAGGTGGCCGTGGGTCTA   80

L  D  V  V  K  A  P  I  G  L  F  G  D  D  A  K  H  E  F  V  T  R  Q  E  Q A
 81  CCTGGACGTCGTGAAGGCCCCGATCGGCCTGTTCGGCGACGATGCCAAACACGAGTTCGTGACCCGTCAGGAACAAGCGG  160
 81  GGACCTGCAGCACTTCCGGGGCTAGCCGGACAAGCCGCTGCTACGGTTTGTGCTCAAGCACTGGGCAGTCCTTGTTCGCC  160

V  S  V  V  S  V  A  V  A  A  G  L  I  C  E  L  I  G  Y  R  G  A  R  S  T  R  Q
161  TCAGCGTTGTCAGCTGGGCGGTTGCGGCCGGTCTGATCTGCGAGCTGATCGGCTACCGTGGTGCGCGC TCGACCCGCCAA  240
161  AGTCGCAACAGTCGACCCGCCAACGCCGGCCAGACTAGACGCTCGACTAGCCGATGGCACCACGCGCG AGCTGGGCGGTT  240

E  Q  A  V  S  V  V  S  V  A  V  A  A  G  L  I  G  E  L  I  G  Y  R  G  A  R  S
241  GAGCAGGCCGTTTCGGTTGTGTCATGGGCCGTGGCAGCAGGTCTGATTGGTGAACTGATTGGTTATCGCGGCGCACGTTC  320
241  CTCGTCCGGCAAAGCCAACACAGTACCCGGCACCGTCGTCCAGACTAACCACTTGACTAACCAATAGCGCCGCGTGCAAG  320

*  *  *  */ *  *  Thr recognition site
          G  R  K  A  I  L  A  N  I   P  F  L  A  I  S  S  L  V  P  R  G  S  R  A  A  A
321  GGGTCGCAAAGCGATCCTGGCCAACATT CCGTTTCTGGCGATCTCGAGCCTGGTGCCGCGCGGCTCCCGGGCTGCAGCTG  400
321  CCCAGCGTTTCGCTAGGACCGGTTGTAA GGCAAAGACCGCTAGAGCTCGGACCACGGCGCGCCGAGGGCCCGACGTCGAC  400
                                        XhoI              Smal  Pst  PvuII G  T  M  E  A  S  H  H  H  H  H  *
401  GTACCATGGAAGCTTCTCACCATCACCATCACCATTAACTTAAG  444
401  CATGGTACCTTCGAAGAGTGGTAGTGGTAGTGGTAATTGAATTC  444
     KpnI NcoI HindIII              AflII
```

EXPRESSION VECTOR CONTAINING THE MAJOR ENVELOPE PROTEIN P9 OF CYSTOVIRUS PHI6 AS A FUSION PARTNER, AND PROCESS FOR PRODUCING A MEMBRANE PROTEIN USING THE SAME

This is a National Phase Application filed under 35 U.S.C. 371 as a national stage of PCT/KR2009/004525, filed on Aug. 13, 2009, and an application claiming foreign priority benefits under 35 USC 119 of Korean Application No. 10-2008-0079542, filed on Aug. 13, 2008, the content of each of which is hereby incorporated by reference in its entirety.

TECHNICAL FIELD

The present invention relates to an expression vector comprising the major envelope protein P9 of Cystovirus phi6 as a fusion partner, a cell transformed by the expression vector and a process for producing a membrane protein by using the transformed cell.

The Sequence Listing submitted in text format (.txt) on Aug. 4, 2011, named "SOPA1001_PCT_US_Sequence_Listing_August4.txt", (created on Thursday, Aug. 4, 2011, 16.7 KB), is incorporated herein by reference.

BACKGROUND OF THE INVENTION

Membrane proteins constitute about 25-30% of the proteome of an organism and participate in basic energy metabolisms such as respiration or photosynthesis, communication between a cell and a cell or between a cell and the outside, material transfer, lipid metabolism, etc. In addition, it was reported that about 50% of commercially available drugs act on a G-protein coupled receptor (GPCR), a kind of membrane proteins, as a working point (Lundstrom, K., *Bioorg. Med. Chem. Lett.*, 15:3654, 2005), and working points of ¼ of the top-selling 100 drugs are GPCR (Klabunde, T. and Hessler, G., *Chem Bio Chem.* 3:928-944, 2002).

However, researches for the functions and structures of membrane proteins fall behind those of water-soluble proteins although membrane proteins are economically important. This is because, unlike water-soluble proteins, it is almost impossible to produce membrane proteins, especially multipass transmembranes, by recombinant DNA techniques (Mancia F. and Hendrickson W. A, *Mol. BioSyst.* 3:723-734, 2007).

Therefore, unlike water-soluble proteins, it is extremely unusual to express membrane proteins by using microorganisms and, moreover, the amount of expressed membrane proteins is very small (Marullo, S. et al., *Proc. Natl. Acd. Sci. USA.*, 85:7551, 1988; Grisshammer et al. *Biochem J.*, 295: 571, 1993). It was reported that about 3 mg per 100 g of *E. coli* cells were obtained through expression of fusion form of a neurotensin receptor and a maltose binding protein, which is the especially successful case (White, J. F., et al. *FEBS Lett.* 564:289, 2004).

However, when the expression of foreign membrane protein is induced through *E. coli*, hosts become dead before the expression of the target protein is observed. In order to solve this problem, the mutant *E. coli* C41 and C43 were developed, which do not die due to inducing expression of membrane protein after introducing a membrane protein expression vector (Miroux, B. and Walker, J. E., *J. Mol. Biol.*, 260:289-298, 1996), and the *E. coli* C41 (DE3) and C43 (DE3) had been used for expression of a membrane protein (Korepanova, A., et al., *Protein Science*, 14:148-158, 2005).

In addition, it was reported that multi-membrane proteins of eukaryotic cells can be expressed by using proteins of *Bacillus subtilus*, called as Mistic, as a fusion partner and, however, it was not effective in expression of membrane proteins (Roosild T. P. et al., *Science*, 307:1317-1321, 2005; Wagner et al., *Trends in Biotech.*, 24:364-371, 2006). Recently, human membrane proteins, such as occluding, claudin 4, ferric reductase and potassium channel, were expressed by using *E. coli* GlpF (glycerol-conducting channel protein) as a fusion partner and, however, this method cannot be applicable when an amino end of a target protein is outside a cell membrane and, in addition, the amount of expression was very small (Neophytou, I. et al., *Appl. Microbiol. Biotechnol.*, 77:375-381, 2007).

Moreover, development of an expression system by using yeasts which have well-developed intracellular membrane systems, has been attempted. Recently, a method for deciding whether or not a membrane protein is expressed by checking the fluorescence of green fluorescent protein (GFP) after inserting a target protein, as a fusional protein with GFP, into a yeast expression vector by using GFP as an expression reporter, was developed (Osterberg M. et al., *Proc. Natl. Acad. Sci.*, 103:11148-11153, 2006; Newstead S. et al., *roc. Natl. Acad. Sci.*, 104:13936-13941, 2007). In this case, the expression rate of proteins derived from animals including a human was very low and the amount of expression thereof was also very small, while the expression rate of yeast-derived proteins was high.

The present inventors has researched into a method for effective expression of membrane proteins of eukaryotic and prokaryotic cells and finally completed the present invention, a method for effective expression of a target membrane protein by combining Cystovirus phi6, a fusion partner, with a major envelope protein P9.

SUMMARY OF THE INVENTION

The object of the present invention is to provide an expression vector which may effectively express a target protein.

The expression vector for expression of a membrane protein comprises a major envelope protein P9 gene of Cystovirus phi6, a multicloning site (MCS) for inserting a target membrane protein, and a protease recognition site located between a P9 gene and the MCS.

Another object of the present invention is to provide a cell transformed by the expression vector Yet another object of the present invention is to provide a process for producing a membrane protein by using the cell.

The process for producing a membrane protein comprises inserting a gene encoding the target membrane protein into the MCS of the expression vector, transforming said gene into a cell, and culturing the transformed cell.

BRIEF DESCRIPTION OF THE DRAWINGS

The objects and features of the present invention will be made clear by the detailed description of the invention with reference to the accompanying figures:

FIG. 1 shows the structure of the membrane protein expression vector pRphi6-9 according to the present invention.

FIG. 2 shows the base sequence list and amino acid sequence list (SEQ ID NO:5) of the P9 protein and the linker-inserted portion out of the expression vector pRphi6-9 of FIG. 1.

Figure 4:
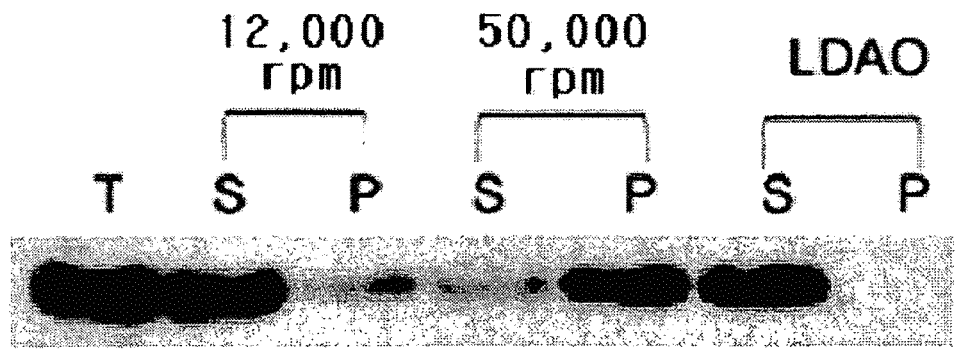

FIG. 4 is the immunoblot result for examining whether or not the P9 protein is inserted into a cell membrane. In this case, T, S and P indicate total protein, supernatants and pellets, respectively.

FIGS. 5 to 8 are the dot blot results for the amounts of expression of A3 adenocine receptor (Adora), endothelin receptor (Endo), lysophosphatidic acid receptor (Lyso), dopamine receptor D2 (Dopa), cysteinyl leukotriene receptor 1 (Leuko), melanocortin 1 receptor (MC1R), prostaglandin E receptor (Prost), neuropeptide Y receptor Y1 (Neuro), serotonin receptor (Sero), thiamine transporter (ThiaT), glucose transporter (GLUT4) and prostaglandin E synthase (mPGES) in E. coli BL21 (DE3) (left) and Rosetta (DE3) (right), respectively, all of which are inserted into the expression vector of FIG. 1.

Figure 9:
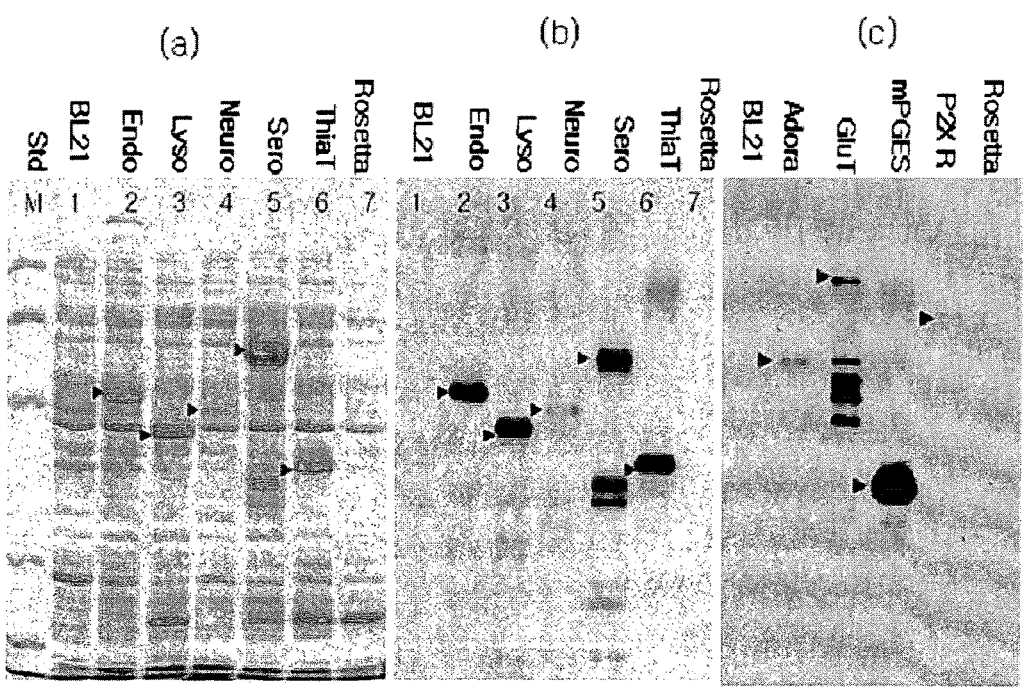

FIG. 9 shows the expression amounts of the above-mentioned eight proteins identified by (a) SDS-PAGE and (b) immunoblot.

Figure 10:
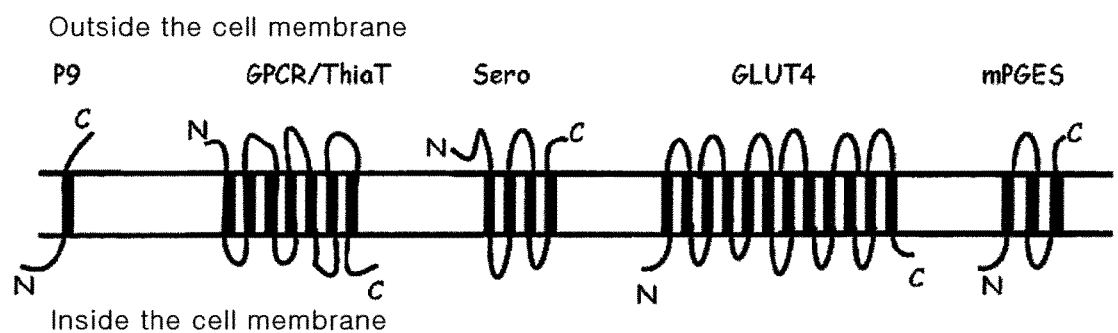

FIG. 10 shows the membrane topology of one of the eight proteins, compared with P9 protein.

Figure 11:
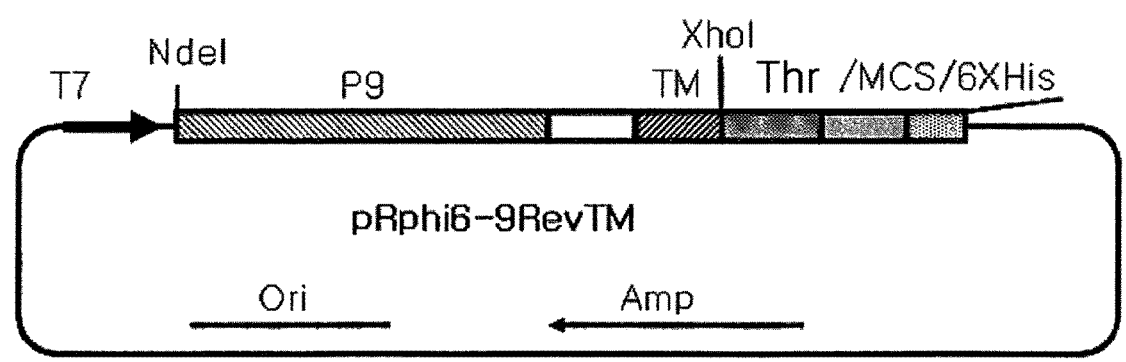

FIG. 11 shows the structure of pRphi6-9RevTM which was produced by inserting an extra transmembrane (TM) domain into XhoI site of the membrane expression vector pRphi6-9 of FIG. 1, thereby having two TM domains of the fusion partner.

FIGS. 12 to 14 show the base sequence list and the amino acid sequence list from the initiation codon of P9 protein to the His tag and the termination codon of P9 protein in the expression vectors, pRphi6-9Rev1TM (SEQ ID NO:36), pRphi6-9Rev2TM (SEQ ID NO:38) and pRphi6-9Rev3TM (SEQ ID NO:40), each of which includes two TM domains.

Figure 15:
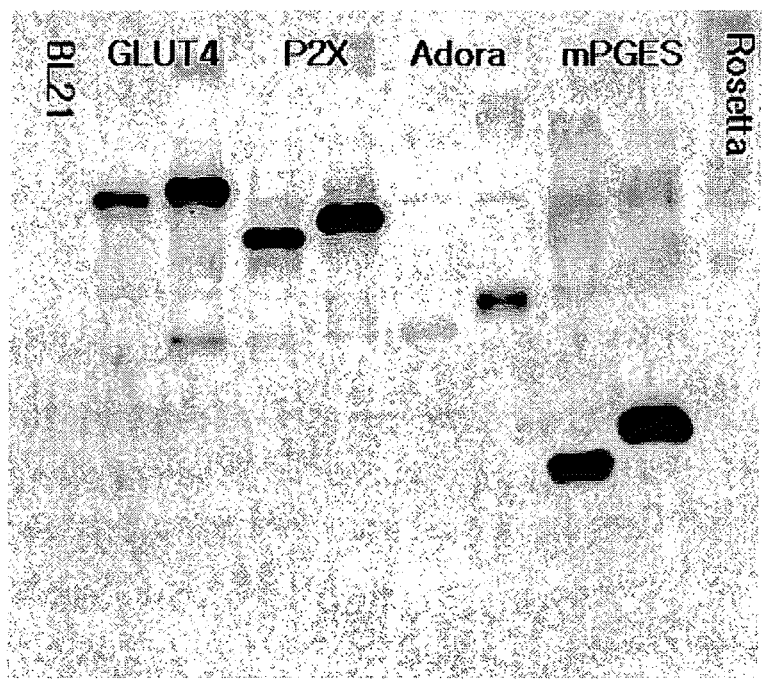

FIG. 15 shows the immunoblot result of the degree of expression of the target proteins, GLUT4, P2X, Adora and mPGES, after SDS-PAGE, in the expression vector pRphi6-9 having one TM domain and the expression vector pRphi6-9Rev1TM having two TM domains. The left and right samples of each protein were obtained from pRphi6-9 vector and pRphi6-9RevTM, respectively.

Figure 16:
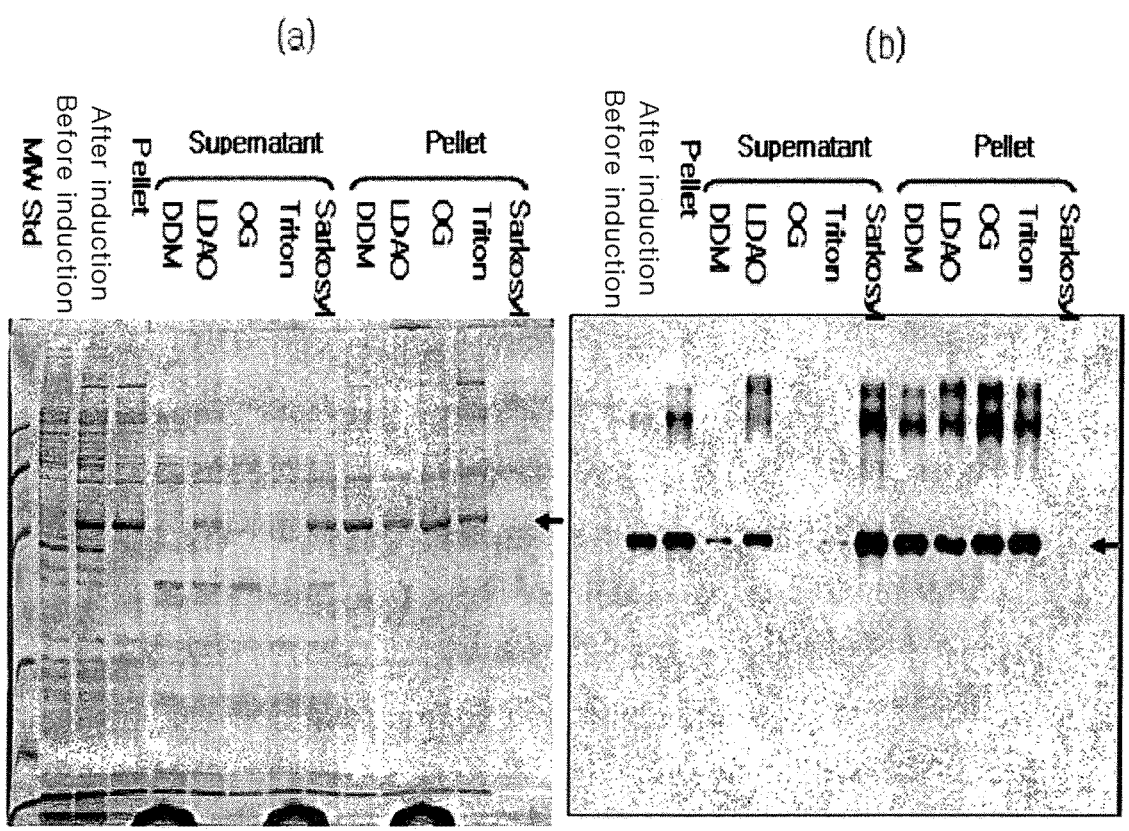

FIG. 16 shows the expression patterns of the overexpressed Endo protein identified by (a) SDS-PAGE and (b) immunoblot after extracting the protein by a solvent, in order to examine whether or not the overexpressed Endo protein is present in the cell membrane.

Figure 17:
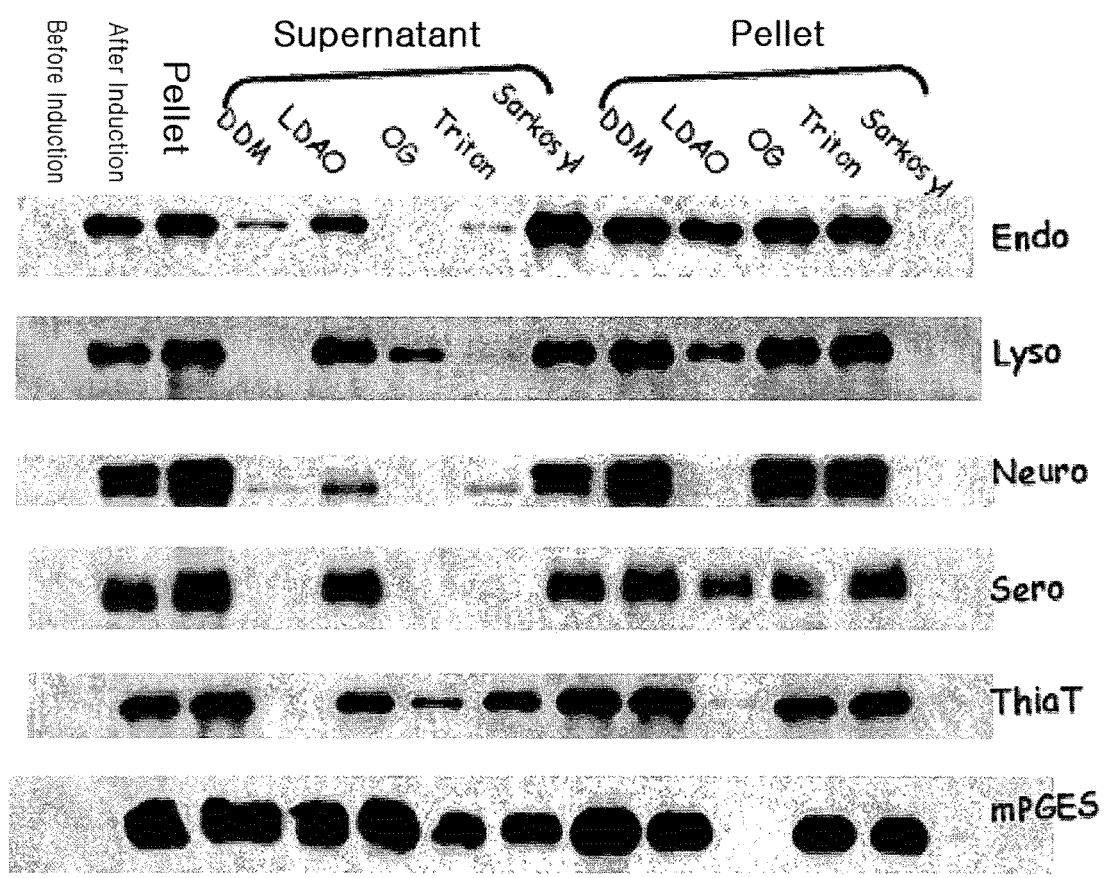

FIG. 17 shows the expression pattern of the overexpressed Endo, Lyso, Neuro, Sero, ThiaT and mPEGS proteins identified by detergent extraction, SDS-PAGE and immunoblot, in order to examine whether or not the overexpressed Endo, Lyso, Neuro, Sero, ThiaT and mPEGS proteins are present in the cell membrane.

Figure 18:
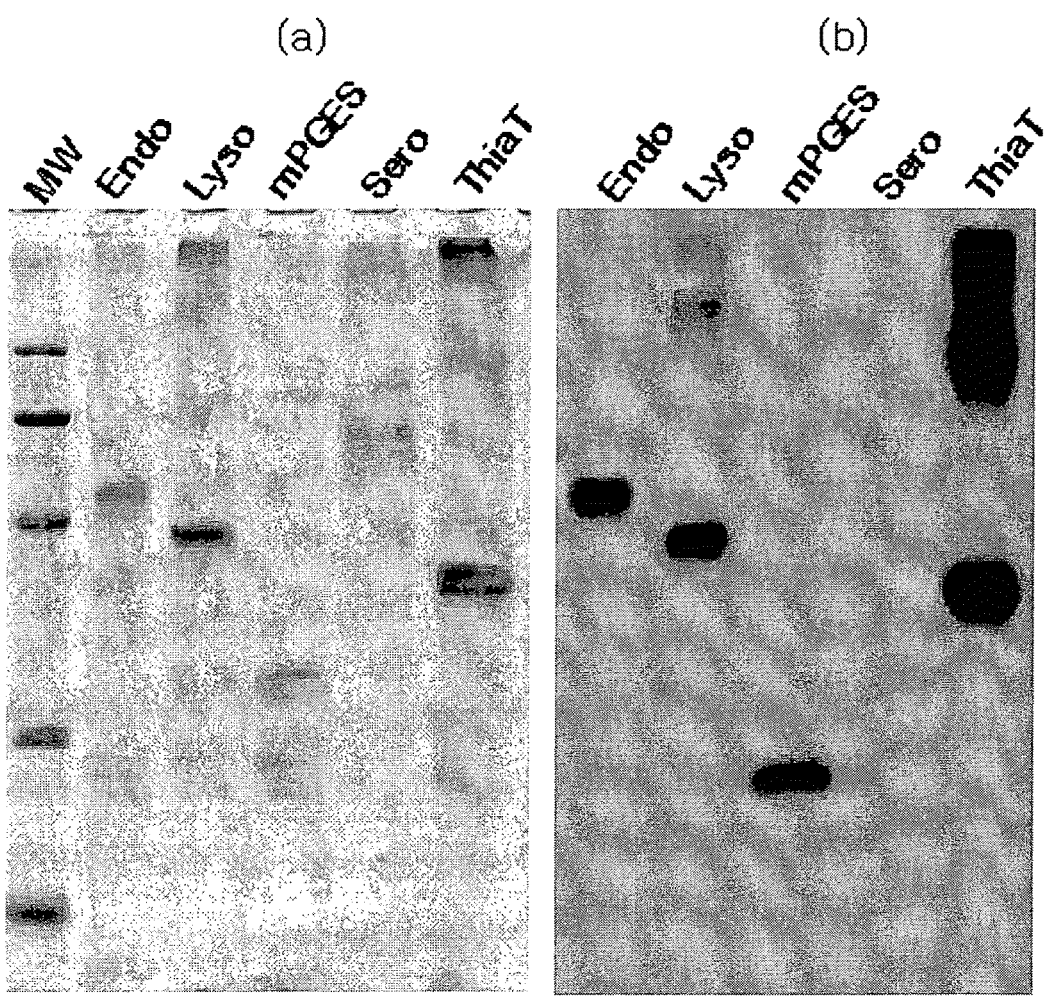

FIG. 18 shows (a) the SDS-PAGE and (b) the immunoblot results of the overexpressed Endo, Lyso, Sero, ThiaT and mPEGS proteins purified by Ni-NTA column.

DETAILED DESCRIPTION OF THE INVENTION

The expression vector according to the present invention is characterized by overexpression of a target membrane protein by using a major envelope protein P9 of Cystovirus phi6 as a fusion partner, and comprises a gene which is joined at and encodes the target membrane protein at 5'-end or 3'-end of the P9 protein encoding gene, thereby expressing the fusion protein which is fused by the target protein at N-terminal or C-terminal of the P9 protein.

The P9 protein may have an amino acid sequence of SEQ ID NO: 1 or SEQ ID NO: 2 and, however, any substitution, addition or deletion of amino acids in the amino acid sequences without influencing the functions of the proteins and, moreover, a part of the proteins may be used or a specific domain may be repeatedly used, as intended. These modified amino acid sequences are also included within the scope of the present invention. Therefore, polypeptides which have substantially the same amino acid sequence as the above-mentioned proteins, and fragments thereof may be used in the present invention, where the substantially the same peptide refers to any peptide having a sequence homology of preferably not less than 80%, more preferably not less than 90% and most preferably not less than 95%.

The gene encoding the protein P9 includes base sequences derived from the amino acid sequences of the protein, according to the genetic code, optimizes codons so as for the genes to be properly expressed in the selected host. Typical examples of these genes include a base sequence of SEQ ID NO: 3 or SEQ ID NO: 4. The base sequences of SEQ ID NO: 3 and SEQ ID NO: 4 encode the amino acid sequences of SEQ ID NO: 1 and SEQ ID NO: 2, respectively.

The expression vector of the present invention may comprise a protease recognition site and a suitable linker DNA which are located between the protein P9 and the site into which a target protein is to be inserted. For example, the expression vector of the present invention may comprise, in the direction of 5' to 3', a promoter, a gene encoding the protein P9, a protease recognition site, a multicloning site (MCS) into which a target protein gene is to be inserted, and a histidin tag, as translational fusion form. In addition, the expression vector of the present invention may additionally comprise an antibiotic resistant gene, if necessary.

Furthermore, the expression vector of the present invention may additionally comprise an extra transmembrane (TM) domain between the P9 protein and the protease recognition site and, when this expression vector is used, expression of membrane proteins which are naturally present within cell membranes may be significantly increased. The extra TM domain which may be added to the expression vector of the present invention may be any TM domain known in the art, for example, a protein P9 of Cystovirus, a protein P10 of Cystovirus, a major coat protein of *Pseudomonas* phage Pf3, a major coat protein of Bacteriophage M13, etc., preferably a TM domain of the protein P9.

In the expression vector of the present invention, the promoter may be T7 promoter, T5 promoter or tac promoter and, however, it is evident for a person skilled in the art that any other suitable promoter which can satisfactorily produce a target protein in the selected host cell. Moreover, the protease may be thrombin, Tev or enterokinase.

In addition, the present invention provides a gene which is manipulated for expressing a target protein as one polypeptide by being fused with a fusion partner derived from Cystovirus. This manipulated fusion gene may produce the target protein by being introduced into bacteria in the form of episome or in the form inserted into a chromosome, or by cell-free protein synthesis in vitro without introducing within a cell.

According to the present invention, the membrane protein may be selected from the group consisting of a membrane receptor, an ion channel, a membrane transporter, a pump, a membrane enzyme, a ligand and a receptor for intercellular communication, a linker for linking cells, a membrane vesicle for intracellular material transport, a ligand and a receptor of endo- and exo-cytosis, a biomembrane protein relating to a viral life cycle, an antibody or a part thereof, and a toxoprotein. For example, the membrane protein may be a human G-protein coupled receptor (GPCR) such as A3 adenosine receptor (Adora: Genbank Accession No. NM_000677), endothelin receptor type A (Endo; Genbank Accession No. BC022511), lysophosphatidic acid receptor 2 (Lyso; Genbank Accession No. BC030615), dopamine receptor D2 (Dopa; Genbank Accession No. BC021195), cysteinyl leukotriene receptor 1 (Leuko; Genbank Accession No. BC035750), melanocortin 1 receptor (MC1R; Genbank Accession No. NM_002386), prostaglandin E receptor 3 (Prost; Genbank Accession No. BC024229); a human multimembrane protein such as neuropeptide Y receptor Y1 (Neuro; Genbank Accession No. BC036657), a solute carrier such as thiamine transporter (ThiaT; Genbank Accession No. BC018514) and a gated ion channel such as serotonin receptor (5-hydroxytryptamine receptor 3A, Sero; Genbank Accession No. BC004453); a solute carrier such as facilitated glucose transporter member 4 (GLUT4; Genbank Accession No. BC014282), and a biomembrane enzyme such as prostaglandin E synthase (mPGES; Genbank Accession No. BC004878).

Moreover, the present invention provides a cell transformed by the expression vector. The cell may be microorganisms such as bacteria, for example, *E. coli, Pseudomonas aeruginosa*, etc., or animal cells.

According to one embodiment of the present invention, the expression vector pRphi6-9 comprising, as a fusion partner, a major envelope protein P9 having an amino acid sequence of SEQ ID NO: 2 was produced (FIGS. 1 and 2), and then *E. coli* BL21 (DE3) or EPI300 was transformed by using the pRphi6-9. The transformed *E. coli* EPI300 strain was named as EPI300/pRphi6-9 and was deposited to the Korean Collection for Type Cultures on Aug. 1, 2008 as the accession number KCTC 11373BP.

Furthermore, the present invention provides a process for producing a target membrane protein comprising inserting a gene encoding the target membrane protein into the MCS of the expression vector, transforming said gene into a cell, and culturing the transformed cell.

According to one embodiment of the present invention, various eukaryote-derived target membrane proteins were inserted into the MCS of the expression vector pRphi6-9 and, then, induced to be overexpressed in *E. coli* (FIGS. 5 to 8). These overexpressed proteins are produced not in the form of an aggregate but in the state of being embedded in a cell membrane since the overexpressed proteins were well extracted by using a moderate solvent such as LDAO (lauryldimethylamine oxide) (FIG. 4). By purifying these overexpressed proteins through Ni-NTA column, it was ascertained that the expression vector of the present invention efficiently expresses various membrane proteins.

Additionally, according to one embodiment of the present invention, the mPGES gene of a membrane protein, for example GLUT4, P2X or Adora, of which N-terminal is naturally present within cell membranes was inserted into the MCS of pRphi6-9RevTM which was produced by adding a TM domain to the expression vector pRphi6-9 and, then, was induced to be expressed in *E. coli*. As a result, it was found that pRphi6-9RevTM expressed the gene not less than five times as much as pRphi6-9 did (FIG. 15).

Although the embodiment of the present invention was carried out by using bacteriophage phi6, it is evident to a person skilled in the art that similar results may be obtained by using a major envelope protein P9 of other bacteriophages which fall under Cystovirus, for example, phi8, phi12, phi13, etc. In addition, although *E. coli* was used as a host cell in the embodiment of the present invention, it is also apparent that other bacteria such as *Pseudomonas aeruginosa* may be used as a host cell.

Additionally, a cell which is produced by the process of the present invention and of which membrane a target protein is expressed, may be utilized for a process for measurement of a membrane protein activity characterized in that such cell is used, and for development of a detection system of ligand-receptor binding.

In addition, antibodies may be produced by recovering the antibodies formed from the immunoreaction induced by administrating a fusion protein of the P9 protein expressed within a biomembrane through the expression vector of the present invention and the target protein, to a vertebrate animal.

Hereinafter, the present invention will be described in greater detail with reference to the following examples. The examples are given only for illustration of the present invention and not to be limiting the present invention.

EXAMPLE 1

Production of Recombinant Vector pRphi6-9 Overexpressing P9 of Cystovirus phi6

In order to produce a recombinant vector overexpressing P9 of Cystovirus phi6, total gene of SEQ ID NO: 4 which encodes the major envelope protein P9 (SEQ ID NO: 2) of phage phi6 was synthesized. At this time, the codons of the synthesized gene were optimized for *E. coli*. The recognition sequence of the restriction enzyme NdeI was inserted near the initiation codon and the recognition sequence of the restriction enzyme XhoI was inserted into the site where the termination codon was removed. In addition, a DNA fragment was synthesized such that a base sequence encoding a thrombin recognition site, MCS, six His codons and a termination codon were positioned next to XhoI in order (refer to SEQ ID NO: 5), and then was inserted into NdeI/HindIII site of a commercially available expression vector pRSET A (Invitrogen), thereby producing the recombinant vector having the structure of FIGS. 1 and 2. These vectors were named as "pRphi6-9."

Figure 3:
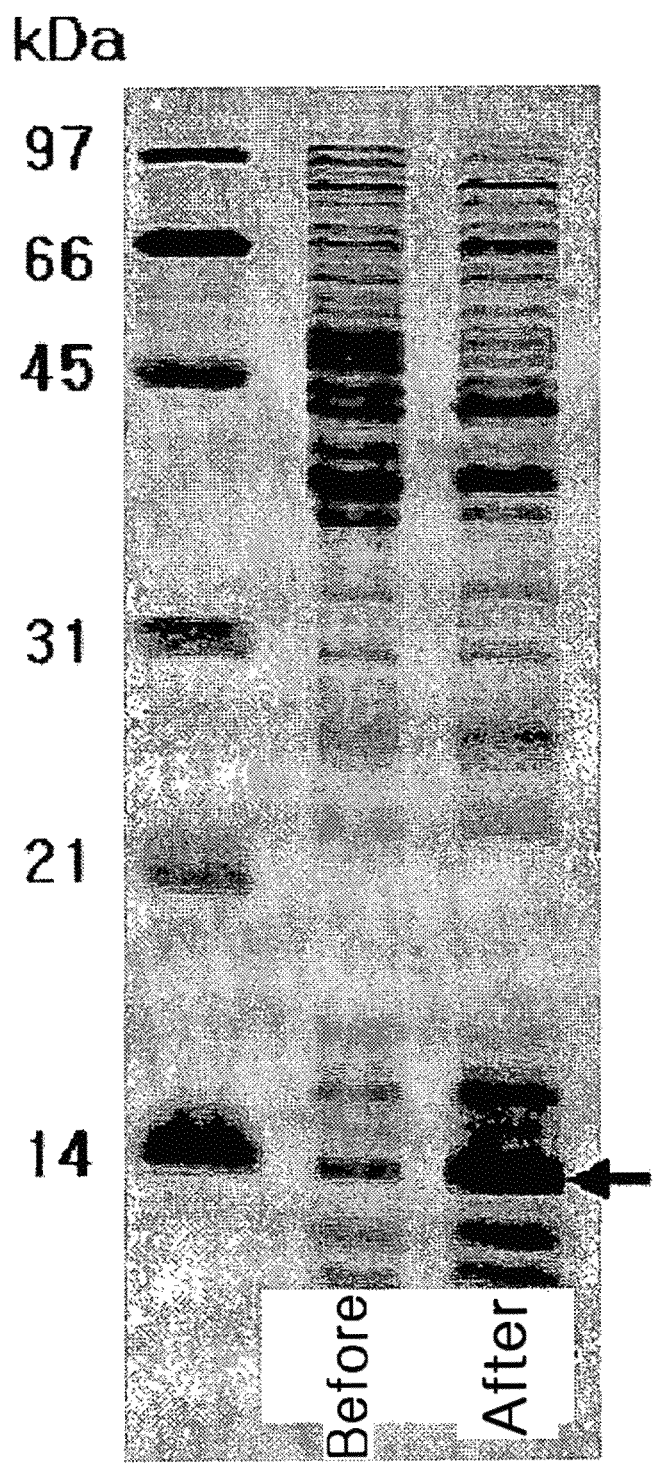
FIG. 3 shows the results of SDS-PAGE of total protein before and after induction of recombinant proteins of *E. coli* transformed by the expression vector of FIG. 1. The arrow indicates the overexpressed P9 protein.

*E. coli* BL21 (DE3) was transformed according to the conventional method by using the vector. It was observed, through electrophoresis (SDS-PAGE) of total proteins obtained by collecting and sonicating *E. coli* cells before and after inducing the expression of the recombinant protein with IPTG, that P9 of about 12 kDa was overexpressed (FIG. 3).

In addition, *E. coli* EPI300 strain (Epicentre, USA) was transformed by the vector pRphi6-9 and the transformed *E. coli* was named as "EPI300/pRphi6-9" which was deposited to the Korean Collection for Type Cultures on Aug. 1, 2008 as the accession number KCTC 11373BP.

EXAMPLE 2

Purification of the Protein P9 of the Phage Phi6 and Production of Antibodies

The transformed *E. coli* produced in Example 1 was sonicated and centrifuged at 12,000 rpm (high speed centrifuge) to obtain the supernatant. Then, the supernatant was centrifuged at 50,000 rpm (ultracentrifuge, 100,000 g) to obtain a precipitate containing cell membrane fragments. Tris-HCl buffer solution (pH 7.5) containing 39 mM LDAO was added to the precipitate and the precipitate was suspended. Then, the suspension was centrifuged at 50,000 rpm and the supernatant was obtained. P9 protein containing His-tag and thrombin recognition site was purified by Ni-NTA-affinity chromatography (Column: H is Trap™ HP (GE Healthcare); mobile phase: 20 mM Tris-HCl buffer solution (pH 7.5) containing 39 mM LDAO; concentration gradient of imidazole: 20~500 mM) and then Superose 6 gel filtration (Column: Superdex™ 75 10/300 GL (GE Healthcare); mobile phase: 20 mM Tris-HCl buffer solution (pH 7.5) containing 13 mM LDAO). Then, antibody was generated by injection of the purified P9 into mice.

Total protein of the transformed *E. coli* was centrifuged at 12,000 rpm and 50,000 rpm, respectively, and supernatants and precipitates were collected. LDAO was added to each of the supernatants and the precipitates, followed by centrifugation. Immunoblot tests were carried out by using the thus obtained supernatants and precipitates and the results are shown in FIG. 4.

As shown in FIG. 4, the generated P9 proteins were present in the supernatant under 12,000 rpm centrifugation, and were precipitated as pellets under 50,000 rpm centrifugation, which were detected in the supernatant after extraction by LDAO and centrifugation. Therefore, it can be understood that the overexpressed P9 proteins were inserted into cell membranes.

EXAMPLE 3

Production of a Human GPCR Expression Plasmid and Expression of GPCR Protein (1)

cDNAs encoding A3 adenosine receptor (Adora: Genbank Accession No. NM_000677), endothelin receptor type A (Endo; Genbank Accession No. BC022511) and lysophosphatidic acid receptor 2 (Lyso; Genbank Accession No. BC030615), which are human GPCRs, were used as templates; SEQ ID NO: 6 and 7, SEQ ID NO: 8 and 9, and SEQ ID NO: 10 and 11 were used as primers for Adora, Endo and Lyso, respectively; and then PCR was performed (94° C. and 3 min, 94° C. and 1 min, 55° C. and 1 min, 72° C. and 1 min, 25 cycles, then 72° C. and 10 min for Adora; 94° C. and 3 min, 94° C. and 1 min, 60° C. and 1 min, 72° C. and 1 min, 25 cycles, then 72° C. and 10 min for Endo and Lyso). The amplified DNA of Adora was cut by restriction enzymes EcoRV and EcoRI, and the amplified DNAs of Endo and Lyso were cut by restriction enzymes PvuII and HindIII, and then the thus obtained DNA fragments were inserted into restriction sites of pRphi6-9 (SmaI/EcoRI for Adora, SmaI/HindIII for Endo and Lyso), thereby producing human GPCR protein expression plasmids which were named "pRphi6-9Adora," "pRphi6-9Endo," and "pRphi6-9Lyso."

*E. coli* hosts, BL21 (DE3) and Rosetta (DE3) (Novagen), which contain T7 RNA polymerase, were transformed by using these expression vectors. While incubating the transformants, protein expression was induced by using IPTG and, then, the expression rate of each GPCR protein was quantified by dot blot, as follows.

Figure 5:
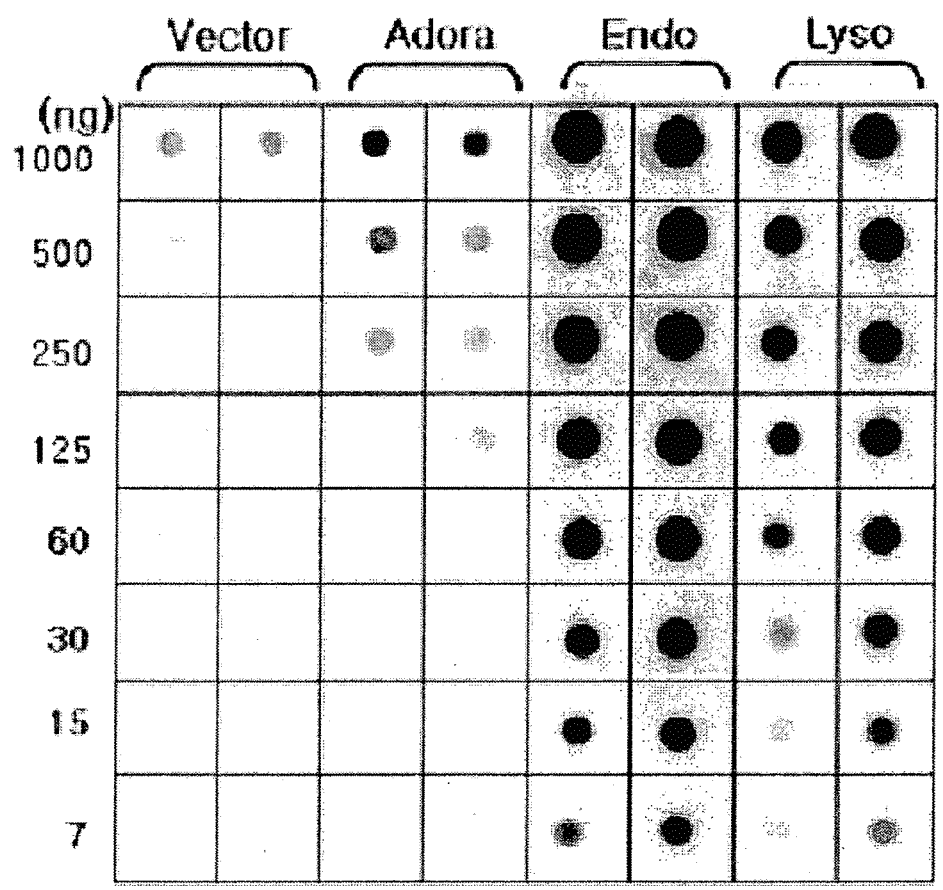

In detail, 100 ng of the P9 proteins of phage phi6, purified in Example 2, was dissolved into a solution and, then, the serial dilutions of the solution (a series of solutions, each of which are half as concentrated (or two times more dilute) than the one from which it was made) were prepared. 1 µl of each of the thus obtained diluted solutions was dropped onto nylon films. Then, each cell which had induced expression of GPCR proteins was collected and sonicated, followed by dissolving to a protein concentration of 1 µg/µl. 1 µl of this total protein extract was serially two-fold diluted and, then, each diluted solution was dropped onto nylon film. After the antibody produced in Example 2 was bonded to the nylon film in a ratio of 1:10,000, the bonded antibody was detected by chemiluminescence and the result is shown in FIG. 5. Samples of each target protein was obtained from BL21 (DE3) (left) and Rosetta (DE3) (right).

As shown in FIG. 5, Adora was expressed, although the expression amount of Adora is small. In addition, when host was BL21 (DE3) or Rosetta (DE3), a maximum 10% or more of total protein was produced in the case of Endo and Lyso.

EXAMPLE 4

Production of a Human GPCR Expression Plasmid and Expression of GPCR Protein (2)

cDNAs encoding dopamine receptor D2 (Dopa; Genbank Accession No. BC021195), cysteinyl leukotriene receptor 1 (Leuko; Genbank Accession No. BC035750), melanocortin 1 receptor (MC1R; Genbank Accession No. NM_002386) and prostaglandin E receptor 3 (Prost; Genbank Accession No. BC024229), which are human GPCRs, were used as templates; SEQ ID NO: 12 and 13, SEQ ID NO: 14 and 15, SEQ ID NO: 16 and 17 and SEQ ID NO: 18 and 19 were used as primers for Dopa, Leuko, MC1R and Prost, respectively; and then PCR was performed (94° C. and 3 min, 94° C. and 1 min, 60° C. and 1 min, 72° C. and 1 min, 28 cycles, then 72° C. and 10 min). The amplified DNAs of Dopa and Leuko were cut by restriction enzymes SmaI/HindIII, and the amplified DNAs of MC1R and Prost were cut by restriction enzymes EcoRV/HindIII, and then each the thus obtained DNA fragments was inserted into the restriction site of pRphi6-9 (SmaI/HindIII), thereby producing human multimembrane protein expression plasmids which were named "pRphi6-9Dopa," "pRphi6-9Leuko," "pRphi6-9MC1R," and "pRphi6-9Prost."

Figure 8:
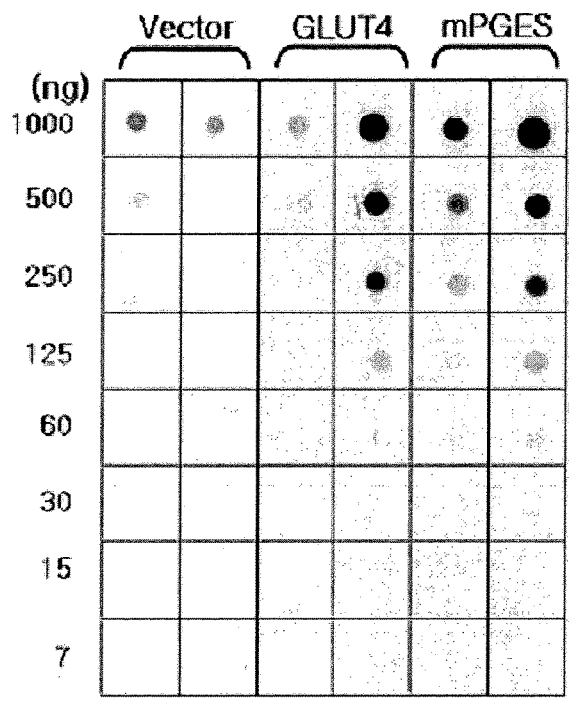

*E. coli* hosts, BL21 (DE3) and Rosetta (DE3), which contain T7 RNA polymerase, were transformed by using these expression vectors. While incubating the transformants, protein expression was induced by using IPTG and, then, the expression rate of each GPCR protein was quantified by the same method as in Example 3. The result is shown in FIG. 8. Samples of each target protein was obtained from BL21 (DE3) (left) and Rosetta (DE3) (right).

Figure 6:
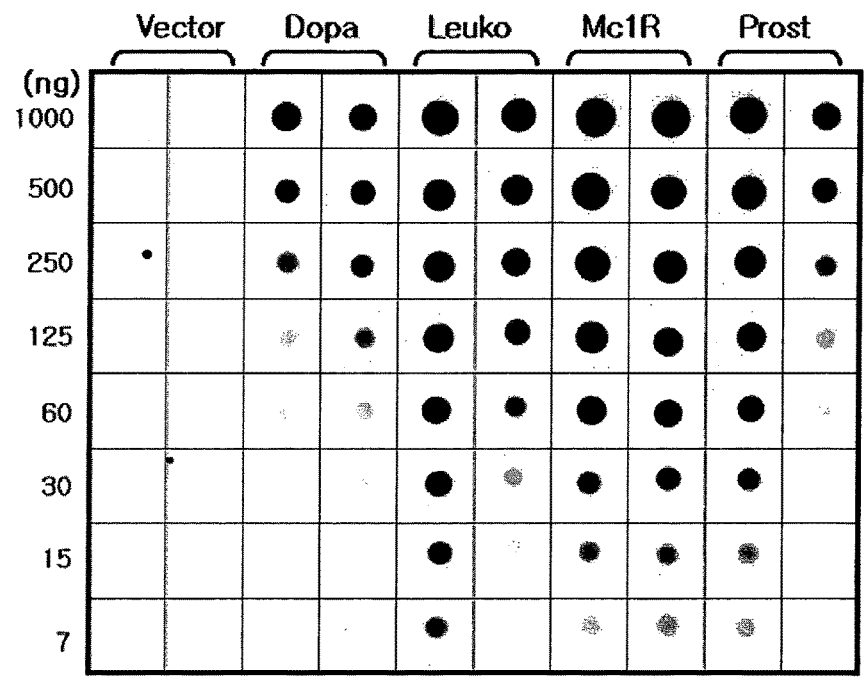

As shown in FIG. 6, Leuko and Prost were maximally expressed at BL21 (DE3) host, while Dopa was maximally expressed at Rosetta (DE3) host. In addition, MC1R protein was highly expressed at both of the hosts.

EXAMPLE 5

Production of Human Multi-Membrane Protein Expression Plasmid and Expression of Proteins (1)

cDNAs encoding a human multi-membrane protein such as neuropeptide Y receptor Y1 (Neuro; Genbank Accession No. BC036657), a solute carrier such as thiamine transporter (ThiaT; Genbank Accession No. BC018514) and a gated ion channel such as serotonin receptor (5-hydroxytryptamine receptor 3A, Sero; Genbank Accession No. BC004453), were used as templates; SEQ ID NO: 20 and 21, SEQ ID NO: 22 and 23, and SEQ ID NO: 24 and 25 were used as primers for Neuro, ThiaT and Sero, respectively; and then PCR was performed (94° C. and 3 min, 94° C. and 1 min, 63° C. and 1 min, 72° C. and 1 min, 25 cycles, then 72° C. and 10 min). The amplified DNAs of Neuro, ThiaT and Sero were cut by restriction enzymes SspI/HindIII, PvuII/HindIII and PvuII/HindIII, respectively, and then each the thus obtained DNA fragments was inserted into the restriction site of pRphi6-9 (SmaI/HindIII), thereby producing human multimembrane protein expression plasmids which were named "pRphi6-9Neuro," "pRphi6-9 ThiaT," "pRphi6-9 Sero," and "pRphi6-9Prost."

Figure 7:
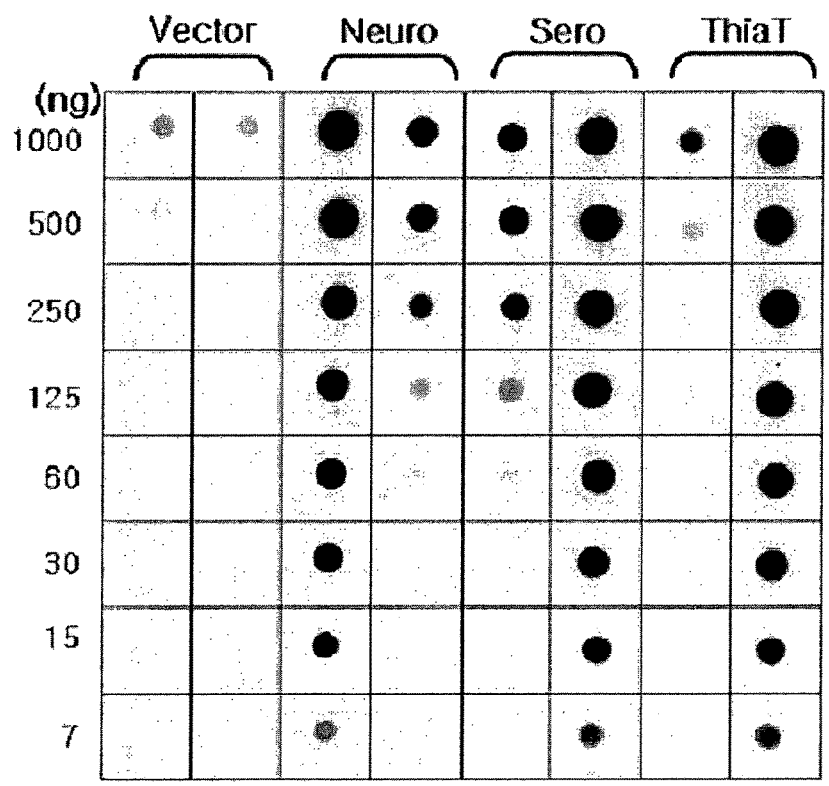

E. coli hosts, BL21 (DE3) and Rosetta (DE3), which contain T7 RNA polymerase, were transformed by using these expression vectors. While incubating the transformants, protein expression was induced by using IPTG and, then, the expression rate of each GPCR protein was quantified by the same method as in Example 3. The result is shown in FIG. 7. Samles of each target protein was obtained from BL21 (DE3) (left) and Rosetta (DE3) (right).

As shown in FIG. 7, Neuro was maximally expressed at BL21 (DE3) host, while ThiaT and Sero were maximally expressed at Rosetta (DE3) host. All the maximum expression amount were measured as 10% or more of total protein.

EXAMPLE 6

Production of Human Multi-Membrane Protein Expression Plasmid and Expression of Proteins (2)

cDNAs encoding a solute carrier such as facilitated glucose transporter member 4 (GLUT4; Genbank Accession No. BC014282), and a biomembrane enzyme such as prostaglandin E synthase (mPGES; Genbank Accession No. BC004878), were used as templates; SEQ ID NO: 26 and 27, and SEQ ID NO: 28 and 29 were used as primers for GLUT4 and mPGES, respectively; and then PCR was performed (94° C. and 3 min, 94° C. and 1 min, 60° C. and 1 min, 72° C. and 1 min, 25 cycles, then 72° C. and 10 min for GLUT4; 94° C. and 3 min, 94° C. and 1 min, 65° C. and 1 min, 72° C. and 1 min, 25 cycles, then 72° C. and 10 min for mPGES). The amplified DNAs of GLUT4 and mPGES were cut by the restriction enzymes EcoRV/HindIII and PvuII/HindIII, respectively, and then each the thus obtained DNA fragments was inserted into the restriction site of pRphi6-9 (SmaI/HindIII), thereby producing human multi-membrane protein expression plasmids which were named "pRphi6-9GLUT4" and "pRphi6-9 mPGES."

E. coli hosts, BL21 (DE3) and Rosetta (DE3), which contain T7 RNA polymerase, were transformed by using these expression vectors. While incubating the transformants, protein expression was induced by using IPTG and, then, the expression rate of each GPCR protein was quantified by the same method as in Example 3. The result is shown in FIG. 8. Samles of each target protein was obtained from BL21 (DE3) (left) and Rosetta (DE3) (right).

As shown in FIG. 8, GLUT4 and mPGES were highly expressed when Rosetta (DE3) was used as a host.

EXAMPLE 7

SDS-PAGE and Immunoblot for Expressed Membrane Protein, and Interrelation Between the Expression Amount and the Membrane Topology In order to examine whether or not the overexpressed proteins are in a normal state, the vectors, pRphi6-9Adora, pRphi6-9Endo and pRphi6-9Neuro, were transformed into the E. coli host, BL21 (DE3), and the vectors, pRphi6-9Lyso, pRphi6-9Sero, pRphi6-9ThiaT and pRphi6-9GLUT4, were transformed into the E. coli host, Rosetta (DE3). Then, while incubating the transformants, protein expression was induced by using IPTG and the expression of each target protein was examined by SDS-PAGE. The detection of the target proteins were carried out by direct observation of protein bands after Coomassie blue staining and by immunoblot using the P9 protein antibody produced in Example 2 and the results are shown in FIG. 9.

As shown in FIG. 9, Endo, Lyso, Neuro, Sero and ThiaT were shown in the deep-colored bands (FIG. 9a) and the proteins corresponding to these bands were confirmed, by immunoblot, to be the target proteins (FIG. 9b). In addition, mPGES was shown in the distinct and complete band having the expected size (FIG. 9c).

Further, in order to find the interrelation between the expression amount of the target protein and the membrane topology, the membrane topologies of the membrane proteins used in Examples 3 to 6 were estimated by using a computer (pubMed, www.ch.embnet.org/software/TMPRED_form-.html; TMMHMM, www.cbs.dtu.dk/services/TMHMM-2.0/; and hmmtop, www.enzim.hu/hmmtop/) and the results were shown in FIG. 10.) and the results were shown in FIG. 10.

As shown in FIG. 10, it can be understood that the target proteins of Examples 3 to 6 have 3 to 12 TM domains and are functional proteins such as GPCRs and membrane enzymes.

EXAMPLE 8

Increase of Membrane Protein Expression by Addition of an Extra TM Domain to the P9 Protein Since it was expected that the C-terminal of a fusion partner would be located within cell membrane when an extra transmembrane domain is added to the fusion partner and, thus, two TM domains exist, a fusion partner having two TM domains was produced as follows.

Firstly, three plasmids for producing P9 mutant protein with reduced C-terminal were produced by PCR. DNA products were obtained after PCR had been performed by using primer pairs (SEQ ID NO: 30 and 31; SEQ ID NO: 30 and 32; and SEQ ID NO: 30 and 33) and pRphi6-9 as a template, thereby producing pRphi6-9Rev1, pRphi6-9Rev2 and pRphi6-9Rev3, respectively, by inserting the DNA products into NdeI/XhoI site of pRphi6-9. These vectors produce P9 proteins in which 4, 9 and 14 C-terminal amino acids are removed, respectively.

Next, in order to insert the sequence from the 48th amino acid to 77th amino acid of the P9 protein including the TM domain (from the 52nd amino acid to 71st amino acid) of the P9 protein (SEQ ID NO: 2), PCR was performed as follows. That is, in order to modify DNA sequence while maintaining the amino acid sequence of the TM domain, SEQ ID NO: 34 including modified codons and SEQ ID NO: 35 including the sequence complimentary to His-tag were used as primers and pRphi6-9 was used as a template, and then PCR (94° C. and 1 min, 94° C. and 30 sec, 72° C. and 1 min, 28 cycles, then 72° C. and 10 min) was carried out, thereby obtaining DNA fragments which contain TM domain, thrombin recognition site, MCS and His-tag. The DNA fragments were cut by using SalI/HindIII and, then, inserted into the XhoI/HindIII site of pRphi6-9Rev1, pRphi6-9Rev2 and pRphi6-9Rev3, respectively, thereby producing the vectors, pRphi6-9Rev1TM (FIG. 12), pRphi6-9Rev2TM (FIG. 13) and pRphi6-9Rev3TM (FIG. 14), all of which have two TM domains. All these three vectors (commonly designated as "pRphi6-9RevTM") have two TM domains and, however, the distance between the two TM domains of each vector is different from one another (FIG. 11). The base sequences of the DNA fragments including the sequence from the initiation codon of P9 to the termination codon next to His-tag, and the amino acid sequences of the proteins encoded by the base sequence, which are included in the vectors, pRphi6-9Rev1TM, pRphi6-9Rev2TM and pRphi6-9Rev3TM, correspond to SEQ ID NO: 36 and 37; SEQ ID NO: 38 and 39; and SEQ ID NO: 40 and 41, respectively.

Adora, GLUT4, mPGES and purinergic receptor P2XR4 (P2X; Genbank Accession No. BC033826) were inserted into each MCS of the three vectors having two TM domains and the expression amounts thereof was compared with the expression amounts obtained by using pRphi6-9. At this time, the XhoI/Hind fragments which were used in Example 3 in the case of Adora and in Example 5 in the case of GLUT4 and mPGES, were inserted into the XhoI/HindIII sites of the 2 TM vectors, pRphi6-9Rev1TM, pRphi6-9Rev2TM and pRphi6-9Rev3TM, respectively. The cDNA clone of P2X was used as a template and SEQ ID NO: 42 and 43 were used as primers, and then PCR (94° C. and 3 min, 94° C. and 1 min, 60° C. and 1 min, 72° C. and 1 min, 25 cycles, then 72° C. and 10 min) was performed. The DNA products obtained by the PCR were cut by using EcoRV/HindIII and the thus obtained fragments were inserted into the SamI/HindIII site of pRphi6-9Rev1TM, pRphi6-9Rev2TM and pRphi6-9Rev3TM.

In order to examine the expression increase due to the extra TM domain, the vector pRphi6-9 in which a target membrane protein was included and the vectors pRphi6-9Rev1TM, pRphi6-9Rev2TM and pRphi6-9Rev3TM in which target membrane proteins are included, were transformed into *E. coli* hosts, BL21 (DE3) and Rosetta (DE3), containing T7 RNA polymerase. Then, while incubating each transformant, protein expression was induced by using IPTG and went through SDS-PAGE according to the conventional method, and then, the expression rate of each target protein was observed via immunoblot by using the P9 protein antibody (FIG. 15). The left samples and right samples of each protein shown in FIG. 15 were derived from the expression vector having one TM domain and two TM domain, respectively, where GLUT4 was expressed from pRphi6-9GLUT4 (left) and pRphi6-9Rev1TMGLUT4 (right), P2X from pRphi6-9P2X (left) and pRphi6-9Rev1TMP2X (right), Adora from pRphi6-9Adora (left) and pRphi6-9Rev2TMAdora (right), mPGES from pRphi6-9 mPGES (left) and pRphi6-9Rev3TMmPGES (right), respectively. Rosetta (DE3) was used as a host for GLUT4, P2X and Adora, and BL21 (DE3) was used for a host for mPGES.

As shown in FIG. 15, as for all the GLUT4, P2X, Adora and mPGES, the amounts of protein expressed by using expression vectors having two TM domains were about five times those of protein expressed by using expression vectors having one TM domain.

EXAMPLE 9

Detergent Extraction of Overexpressed Membrane Proteins

In order to examine whether the membrane protein expressed by the present invention is present within cell membrane, as is naturally the case, or present as a functionless aggregate, detergent extraction of the expressed proteins was performed.

In detail, after *E. coli* cells containing the overexpressed protein, Endo, which was produced in Examples 3 to 5 were sonicated, precipitates were collected by ultracentrifugation thereof for 1 hour at 100,000 g, and then the detergents, DDM (n-dodecyl-β-D-maltoside), LDAO, OG (n-octyl-beta-D-glucopyranoside), Triton X100 and sarkosyl, were added to the precipitates, thereby extracting the membrane protein. After detergent was added to the extracted membrane protein, the thus obtained suspension was separated into the supernatant and precipitate by ultracentrifugation at 100,000 g. The supernatant and precipitate were subject to SDS-PAGE according to the conventional method and, then, the target proteins were detected by the Coomassie blue-staining and the immunoblot. The results are shown in FIG. 16.

As shown in FIG. 16, it can be understood that the overexpressed Endo is present, being inserted into cell membranes in that the overexpressed Endo was extracted by the detergent.

In addition, it was also examined whether or not other membrane proteins are present within cell membranes according to the same method as described above, and the results are shown in FIG. 17.

As shown in FIG. 17, when sarkosyl was used, all the overexpressed proteins were extracted to the supernatant. When LDAO was used, 90% or more of mPGES and ThiaT, about 75% of Lyso and Sero, and about 50% of Endo were extracted to the supernatant. Moreover, considerable portion of the overexpressed proteins were extracted to Triton X100 (mPGES and ThiaT) or OG (Lyso), to a certain extent. It can be seen that all of the 6 overexpressed membrane proteins are in the state of insertion into cell membranes in that the target proteins were extracted to such a moderate detergents.

EXAMPLE 10

Purification of the Overexpressed Membrane Proteins

The proteins, Endo, Lyso, mPGES, Sero and ThiaT were purified by using the vector of the present invention, after overexpression.

In detail, BL21 (DE3) cells, produced in Examples 3 to 5, which include the expression plasmids of the above-mentioned proteins were incubated in the culture medium (Difco LB broth) at 25° C. until the optical density (O.D.) became 0.8, and then ITPG was added, followed by additional incubation for 6 hr. After collecting the cells, the cell were dissolved in sonication buffer (20 mM Tris-Cl, pH 8.0, 0.3 M NaCl and 10% glycerol) and sonicated. Precipitates were collected after centrifugation of the sonicated solution at 100,000 g for 1 hr. The precipitates were dissolved in sonification buffer containing 39 mM of LDAO, followed by centrifugation at 100,000 g for 1 hr, and the supernatant to which the target proteins were extracted was obtained. Imidazole was added to the supernatant so as to be a concentration of 10 mM and, then, the thus obtained solution was subject to Ni-NTA column chromatography. After sufficiently washing the column with a loading buffer (20 mM Tris-HCl, pH 8.0, 0.3 M NaCl, 10% glycerol and 5 mM imidazole), the target proteins were separated from the colmn by employing an imidazole concentration gradient (10 mM to 500 mM). The separated proteins were examined by SDS-PAGE and immunoblot and the results are shown in FIG. 18.

As shown in FIG. 18, all the 5 target proteins were efficiently overexpressed such that the proteins were significantly purified by using only one Ni-NTA column.

The present invention has been described with reference to specific examples and, however, it should be noted that a person skilled in the art can modify or vary the present invention defined by the accompanying claims within the scope of the invention.

The invention claimed is:

1. An expression vector comprising a major envelope protein P9 gene of Cystovirus phi6, a multicloning site (MCS) for inserting a target membrane protein, and a protease recognition site located between a P9 gene and the MCS.

2. The expression vector of claim 1, wherein said major envelope protein P9 has the amino acid sequence of SEQ ID NO: 1 or SEQ ID NO: 2.

3. The expression vector of claim 1, wherein said major envelope protein P9 has the nucleotide sequence of SEQ ID NO: 3 or SEQ ID NO: 4.

4. The expression vector of claim 1, wherein said expression vector comprises a promoter, a protein P9 gene, a protease recognition site, an MCS and a histidine tag which are linked in a 5'- to 3'-direction in the form of being fused to a translational fusion.

5. The expression vector of claim 4, wherein said expression vector has the nucleotide sequence of SEQ ID NO: 5.

6. The expression vector of claim 4, wherein said expression vector additionally comprises an extra transmembrane (TM) domain between said protein P9 gene and said protease recognition site.

7. The expression vector of claim 6, wherein said extra TM domain is derived from a TM domain-containing protein selected from the group consisting of a protein P9 of Cystovirus, a protein P10 of Cystovirus, a major coat protein of *Pseudomonas* phage Pf3 and a major coat protein of Bacteriophage M13.

8. The expression vector of claim 6, wherein said expression vector comprises a base sequence which encodes a protein of SEQ ID NO: 37, 39 or 41.

9. The expression vector of claim 8, wherein said a nucleotide sequence is selected from the group consisting of SEQ ID NO: 36, SEQ ID NO: 38 and SEQ ID NO: 40.

10. The expression vector of claim 4, wherein said promoter is selected from the group consisting of T7 promoter, T5 promoter and tac promoter.

11. The expression vector of claim 4, wherein said protease is selected from the group consisting of thrombin, Tev and enterokinase.

12. The expression vector of claim 1, wherein said expression vector is pRphi6-9 (Depository number: KCTC 11373BP).

13. A cell transformed by the expression vector in claim 1.

14. The cell of claim 13, wherein said cell is a cell of a microorganism or an animal.

15. The cell of claim 13, wherein said cell is *Escherichia coli* EPI300/pRphi6-9 (Depository number: KCTC 11373BP).

16. A process for producing a target membrane protein comprising inserting a gene encoding the target membrane protein into the MCS of the expression vector of claim 1, transforming said gene into a cell, and culturing the transformed cell.

17. The process of claim 16, wherein said membrane protein is selected from the group consisting of a membrane receptor, an ion channel, a membrane transporter, a pump, a membrane enzyme, a ligand and a receptor for intercellular communication, a linker for linking cells, a membrane vesicle for intracellular material transport, a ligand and a receptor of endo- and exo-cytosis, a biomembrane protein relating to a viral life cycle, an antibody or a part thereof, and a toxoprotein.

* * * * *

UNITED STATES PATENT AND TRADEMARK OFFICE
CERTIFICATE OF CORRECTION

PATENT NO. : 8,628,939 B2  
APPLICATION NO. : 13/058425  
DATED : January 14, 2014  
INVENTOR(S) : Lim et al.

Page 1 of 1

It is certified that error appears in the above-identified patent and that said Letters Patent is hereby corrected as shown below:

In the Claims

-Claim 9, Column 32, Line 1, after "said" and before "Nucleotide"

Please delete "a"

Signed and Sealed this  
Tenth Day of June, 2014

Michelle K. Lee  
*Deputy Director of the United States Patent and Trademark Office*

SEQUENCE LISTING

<160> NUMBER OF SEQ ID NOS: 43

<210> SEQ ID NO 1
<211> LENGTH: 90
<212> TYPE: PRT
<213> ORGANISM: Artificial Sequence
<220> FEATURE:
<223> OTHER INFORMATION: Wild type P9 protein of Cystovirus phi6

<400> SEQUENCE: 1

Met Pro Phe Pro Leu Val Lys Gln Asp Pro Thr Ser Lys Ala Phe Thr
 1               5                  10                  15

Glu Ala Ser Glu Arg Ser Thr Gly Thr Gln Ile Leu Asp Val Val Lys
            20                  25                  30

Ala Pro Ile Gly Leu Phe Gly Asp Asp Ala Lys His Glu Phe Val Thr
        35                  40                  45

Arg Gln Glu Gln Ala Val Ser Val Val Ser Trp Ala Val Ala Ala Gly
    50                  55                  60

Leu Ile Gly Glu Leu Ile Gly Tyr Arg Gly Ala Arg Ser Gly Arg Lys
65                  70                  75                  80

Ala Ile Leu Ala Asn Ile Pro Phe Leu Ala
            85                  90

<210> SEQ ID NO 2
<211> LENGTH: 90
<212> TYPE: PRT
<213> ORGANISM: Artificial Sequence
<220> FEATURE:
<223> OTHER INFORMATION: Mutant P9 protein of Cystovirus phi6
<220> FEATURE:
<221> NAME/KEY: VARIANT
<222> LOCATION: (67)
<223> OTHER INFORMATION: 67th glycine is changed to cystein

<400> SEQUENCE: 2

Met Pro Phe Pro Leu Val Lys Gln Asp Pro Thr Ser Lys Ala Phe Thr
 1               5                  10                  15

Glu Ala Ser Glu Arg Ser Thr Gly Thr Gln Ile Leu Asp Val Val Lys
            20                  25                  30

Ala Pro Ile Gly Leu Phe Gly Asp Asp Ala Lys His Glu Phe Val Thr
        35                  40                  45

Arg Gln Glu Gln Ala Val Ser Val Val Ser Trp Ala Val Ala Ala Gly
    50                  55                  60

Leu Ile Cys Glu Leu Ile Gly Tyr Arg Gly Ala Arg Ser Gly Arg Lys
65                  70                  75                  80

Ala Ile Leu Ala Asn Ile Pro Phe Leu Ala
            85                  90

<210> SEQ ID NO 3
<211> LENGTH: 273
<212> TYPE: DNA
<213> ORGANISM: Artificial Sequence
<220> FEATURE:
<223> OTHER INFORMATION: Wild type P9 protein of Cystovirus phi6

<400> SEQUENCE: 3
atgccatttc ctctggtaaa gcaagaccca acctcgaagg ctttcactga agccagtgaa      60
cgctccaccg gcacccagac cctggacgtc gtcaaggccc ctatcggcct gttcggcgac     120
gatgccaaac acgagttcgt gaccgtcag gaacaagccg tctccgtcgt cagctgggca     180

```
gttgctgccg gtctgatcgg cgagctgatc ggctaccgtg gtgcgcgttc gggtcgcaaa      240
gcgatcctgg ccaacatccc tttcctggcc taa                                   273
```

<210> SEQ ID NO 4
<211> LENGTH: 273
<212> TYPE: DNA
<213> ORGANISM: Artificial Sequence
<220> FEATURE:
<223> OTHER INFORMATION: Mutant P9 protein of Cystovirus phi6

<400> SEQUENCE: 4

```
atgccgtttc cgctggtgaa acaggacccg accagcaaag cgttcaccga agccagcgaa      60
cgctccaccg gcacccagat cctggacgtc gtgaaggccc cgatcggcct gttcggcgac      120
gatgccaaac acgagttcgt gacccgtcag gaacaagcgg tcagcgttgt cagctgggcg      180
gttgcggccg gtctgatctg cgagctgatc ggctaccgtg gtgcgcgctc gggtcgcaaa      240
gcgatcctgg ccaacattcc gtttctggcg taa                                   273
```

<210> SEQ ID NO 5
<211> LENGTH: 348
<212> TYPE: DNA
<213> ORGANISM: Artificial Sequence
<220> FEATURE:
<223> OTHER INFORMATION: pRphi6-9 plasmid comprising start codon, p9DNA,
      XhoI site, thrombin site, polylinker, 6XHis and stop codon

<400> SEQUENCE: 5

```
atgccgtttc cgctggtgaa acaggacccg accagcaaag cgttcaccga agccagcgaa      60
cgctccaccg gcacccagat cctggacgtc gtgaaggccc cgatcggcct gttcggcgac      120
gatgccaaac acgagttcgt gacccgtcag gaacaagcgg tcagcgttgt cagctgggcg      180
gttgcggccg gtctgatctg cgagctgatc ggctaccgtg gtgcgcgctc gggtcgcaaa      240
gcgatcctgg ccaacattcc gtttctggcg atctcgagcc tggtgccgcg cggctcccgg      300
gctgcagctg gtaccatgga agcttctcac catcaccatc accattaa                   348
```

<210> SEQ ID NO 6
<211> LENGTH: 32
<212> TYPE: DNA
<213> ORGANISM: Artificial Sequence
<220> FEATURE:
<223> OTHER INFORMATION: forward primer for Adora

<400> SEQUENCE: 6

```
aagctgcaga tatccccaac aacagcactg ct                                    32
```

<210> SEQ ID NO 7
<211> LENGTH: 31
<212> TYPE: DNA
<213> ORGANISM: Artificial Sequence
<220> FEATURE:
<223> OTHER INFORMATION: reverse primer for Adora

<400> SEQUENCE: 7

```
ggggtaccaa ttgctactca gaattcttct c                                     31
```

<210> SEQ ID NO 8
<211> LENGTH: 28
<212> TYPE: DNA
<213> ORGANISM: Artificial Sequence
<220> FEATURE:
<223> OTHER INFORMATION: forward primer for Endo

<400> SEQUENCE: 8

```
tgaccagctg aaacccttcg cctcaggg                                          28

<210> SEQ ID NO 9
<211> LENGTH: 30
<212> TYPE: DNA
<213> ORGANISM: Artificial Sequence
<220> FEATURE:
<223> OTHER INFORMATION: reverse primer for Endo

<400> SEQUENCE: 9
agctaagctt ggttcatgct gtccttatgg                                        30

<210> SEQ ID NO 10
<211> LENGTH: 32
<212> TYPE: DNA
<213> ORGANISM: Artificial Sequence
<220> FEATURE:
<223> OTHER INFORMATION: forward primer for Lyso

<400> SEQUENCE: 10
tgaccagctg ctgccatctc tacttccatc cc                                     32

<210> SEQ ID NO 11
<211> LENGTH: 30
<212> TYPE: DNA
<213> ORGANISM: Artificial Sequence
<220> FEATURE:
<223> OTHER INFORMATION: reverse primer for Lyso

<400> SEQUENCE: 11
agctaagctt gaaccacaga gtggtcattg                                        30

<210> SEQ ID NO 12
<211> LENGTH: 29
<212> TYPE: DNA
<213> ORGANISM: Artificial Sequence
<220> FEATURE:
<223> OTHER INFORMATION: forward primer for Dopa

<400> SEQUENCE: 12
cccgggtgga tccactgaat ctgtcctgg                                         29

<210> SEQ ID NO 13
<211> LENGTH: 28
<212> TYPE: DNA
<213> ORGANISM: Artificial Sequence
<220> FEATURE:
<223> OTHER INFORMATION: reverse primer for Dopa

<400> SEQUENCE: 13
aagcttcgca gtggaggatc ttcaggaa                                          28

<210> SEQ ID NO 14
<211> LENGTH: 29
<212> TYPE: DNA
<213> ORGANISM: Artificial Sequence
<220> FEATURE:
<223> OTHER INFORMATION: forward primer for Leuko

<400> SEQUENCE: 14
cccgggacga tgaaacagga aatctgaca                                         29

<210> SEQ ID NO 15
<211> LENGTH: 28
<212> TYPE: DNA
<213> ORGANISM: Artificial Sequence
```

```
<220> FEATURE:
<223> OTHER INFORMATION: reverse primer for Leuko

<400> SEQUENCE: 15
aagcttctac tttacatatt tcttctcc                                              28

<210> SEQ ID NO 16
<211> LENGTH: 29
<212> TYPE: DNA
<213> ORGANISM: Artificial Sequence
<220> FEATURE:
<223> OTHER INFORMATION: forward primer for MC1R

<400> SEQUENCE: 16
gatatcctgc tgtgcaggga tcccagaga                                             29

<210> SEQ ID NO 17
<211> LENGTH: 28
<212> TYPE: DNA
<213> ORGANISM: Artificial Sequence
<220> FEATURE:
<223> OTHER INFORMATION: reverse primer for MC1R

<400> SEQUENCE: 17
aagcttccca ggagcacgtc agcacctc                                              28

<210> SEQ ID NO 18
<211> LENGTH: 29
<212> TYPE: DNA
<213> ORGANISM: Artificial Sequence
<220> FEATURE:
<223> OTHER INFORMATION: forward primer for Prost

<400> SEQUENCE: 18
gatatcacaa ggagacccgg ggctacgga                                             29

<210> SEQ ID NO 19
<211> LENGTH: 28
<212> TYPE: DNA
<213> ORGANISM: Artificial Sequence
<220> FEATURE:
<223> OTHER INFORMATION: reverse primer for Prost

<400> SEQUENCE: 19
aagcttcatt tccccaaaat tcctcttg                                              28

<210> SEQ ID NO 20
<211> LENGTH: 29
<212> TYPE: DNA
<213> ORGANISM: Artificial Sequence
<220> FEATURE:
<223> OTHER INFORMATION: forward primer for Neuro

<400> SEQUENCE: 20
atgacaatat tcaacattat tttcccagg                                             29

<210> SEQ ID NO 21
<211> LENGTH: 32
<212> TYPE: DNA
<213> ORGANISM: Artificial Sequence
<220> FEATURE:
<223> OTHER INFORMATION: reverse primer for Neuro

<400> SEQUENCE: 21
agctaagctt gatttttca ttatcatcat tg                                          32
```

```
<210> SEQ ID NO 22
<211> LENGTH: 27
<212> TYPE: DNA
<213> ORGANISM: Artificial Sequence
<220> FEATURE:
<223> OTHER INFORMATION: forward primer for ThiaT

<400> SEQUENCE: 22
gacagctgat gtgcccggcc cggtgtc                                27

<210> SEQ ID NO 23
<211> LENGTH: 30
<212> TYPE: DNA
<213> ORGANISM: Artificial Sequence
<220> FEATURE:
<223> OTHER INFORMATION: reverse primer for ThiaT

<400> SEQUENCE: 23
ggaagcttct gaagtggtta cttgagaact                             30

<210> SEQ ID NO 24
<211> LENGTH: 28
<212> TYPE: DNA
<213> ORGANISM: Artificial Sequence
<220> FEATURE:
<223> OTHER INFORMATION: forward primer for Sero

<400> SEQUENCE: 24
gacagctgtg ctgctgtggg tccagcag                               28

<210> SEQ ID NO 25
<211> LENGTH: 30
<212> TYPE: DNA
<213> ORGANISM: Artificial Sequence
<220> FEATURE:
<223> OTHER INFORMATION: reverse primer for Sero

<400> SEQUENCE: 25
ggaagcttca gcgtactgcc agatggacca                             30

<210> SEQ ID NO 26
<211> LENGTH: 28
<212> TYPE: DNA
<213> ORGANISM: Artificial Sequence
<220> FEATURE:
<223> OTHER INFORMATION: forward primer for GLUT4

<400> SEQUENCE: 26
gagatatctg ccgtcgggtt tccagcag                               28

<210> SEQ ID NO 27
<211> LENGTH: 30
<212> TYPE: DNA
<213> ORGANISM: Artificial Sequence
<220> FEATURE:
<223> OTHER INFORMATION: reverse primer for GLUT4

<400> SEQUENCE: 27
ggaagcttcg tcattctcat ctggccctaa                             30

<210> SEQ ID NO 28
<211> LENGTH: 29
<212> TYPE: DNA
<213> ORGANISM: Artificial Sequence
<220> FEATURE:
<223> OTHER INFORMATION: forward primer for mPGES

<400> SEQUENCE: 28
```

```
gacagctgtg cctgcccaca gcctggtga                                      29
```

<210> SEQ ID NO 29
<211> LENGTH: 30
<212> TYPE: DNA
<213> ORGANISM: Artificial Sequence
<220> FEATURE:
<223> OTHER INFORMATION: reverse primer for mPGES

<400> SEQUENCE: 29

```
ggaagcttcc aggtggcggg ccgcttccca                                     30
```

<210> SEQ ID NO 30
<211> LENGTH: 22
<212> TYPE: DNA
<213> ORGANISM: Artificial Sequence
<220> FEATURE:
<223> OTHER INFORMATION: forward primer for mutant P9 protein

<400> SEQUENCE: 30

```
ggagatatac atatgccgtt tc                                             22
```

<210> SEQ ID NO 31
<211> LENGTH: 26
<212> TYPE: DNA
<213> ORGANISM: Artificial Sequence
<220> FEATURE:
<223> OTHER INFORMATION: reverse primer for mutant P9 protein, Rev1

<400> SEQUENCE: 31

```
cctcgagatg ttggccagga tcgctt                                         26
```

<210> SEQ ID NO 32
<211> LENGTH: 26
<212> TYPE: DNA
<213> ORGANISM: Artificial Sequence
<220> FEATURE:
<223> OTHER INFORMATION: reverse primer for mutant P9 protein, Rev2

<400> SEQUENCE: 32

```
cctcgaggct ttgcgacccg agcgcg                                         26
```

<210> SEQ ID NO 33
<211> LENGTH: 26
<212> TYPE: DNA
<213> ORGANISM: Artificial Sequence
<220> FEATURE:
<223> OTHER INFORMATION: reverse primer for mutant P9 protein, Rev3

<400> SEQUENCE: 33

```
cctcgagcgc gcaccacggt agccga                                         26
```

<210> SEQ ID NO 34
<211> LENGTH: 107
<212> TYPE: DNA
<213> ORGANISM: Artificial Sequence
<220> FEATURE:
<223> OTHER INFORMATION: forward primer for extra TM

<400> SEQUENCE: 34

```
gttgtcgacc cgccaagagc aggccgtttc ggttgtgtca tgggccgtgg cagcaggtct    60
gattggtgaa ctgattggtt atcgcggcgc acgttcgggt cgcaaag                 107
```

<210> SEQ ID NO 35
<211> LENGTH: 45

-continued

<212> TYPE: DNA
<213> ORGANISM: Artificial Sequence
<220> FEATURE:
<223> OTHER INFORMATION: reverse primer for extra TM

<400> SEQUENCE: 35
agctccggac ttaagttaat ggtgatggtg atggtgagaa gcttc        45

<210> SEQ ID NO 36
<211> LENGTH: 474
<212> TYPE: DNA
<213> ORGANISM: Artificial Sequence
<220> FEATURE:
<223> OTHER INFORMATION: pRphi6-9Rev1TM

<400> SEQUENCE: 36
atgccgtttc cgctggtgaa acaggacccg accagcaaag cgttcaccga agccagcgaa        60
cgctccaccg gcacccagat cctggacgtc gtgaaggccc cgatcggcct gttcggcgac       120
gatgccaaac acgagttcgt gacccgtcag gaacaagcgg tcagcgttgt cagctgggcg       180
gttgcggccg gtctgatctg cgagctgatc ggctaccgtg gtgcgcgctc gggtcgcaaa       240
gcgatcctgg ccaacatctc gacccgccaa gagcaggccg tttcggttgt gtcatgggcc       300
gtggcagcag gtctgattgg tgaactgatt ggttatcgcg gcgcacgttc gggtcgcaaa       360
gcgatcctgg ccaacattcc gtttctggcg atctcgagcc tggtgccgcg cggctcccgg       420
gctgcagctg gtaccatgga agcttctcac catcaccatc accattaact taag            474

<210> SEQ ID NO 37
<211> LENGTH: 155
<212> TYPE: PRT
<213> ORGANISM: Artificial Sequence
<220> FEATURE:
<223> OTHER INFORMATION: pRphi6-9Rev1TM

<400> SEQUENCE: 37

Met Pro Phe Pro Leu Val Lys Gln Asp Pro Thr Ser Lys Ala Phe Thr
 1               5                  10                  15

Glu Ala Ser Glu Arg Ser Thr Gly Thr Gln Ile Leu Asp Val Val Lys
            20                  25                  30

Ala Pro Ile Gly Leu Phe Gly Asp Asp Ala Lys His Glu Phe Val Thr
        35                  40                  45

Arg Gln Glu Gln Ala Val Ser Val Ser Trp Ala Val Ala Ala Gly
    50                  55                  60

Leu Ile Cys Glu Leu Ile Gly Tyr Arg Gly Ala Arg Ser Gly Arg Lys
65                  70                  75                  80

Ala Ile Leu Ala Asn Ile Ser Thr Arg Gln Glu Gln Ala Val Ser Val
                85                  90                  95

Val Ser Trp Ala Val Ala Ala Gly Leu Ile Gly Glu Leu Ile Gly Tyr
           100                 105                 110

Arg Gly Ala Arg Ser Gly Arg Lys Ala Ile Leu Ala Asn Ile Pro Phe
       115                 120                 125

Leu Ala Ile Ser Ser Leu Val Pro Arg Gly Ser Arg Ala Ala Ala Gly
   130                 135                 140

Thr Met Glu Ala Ser His His His His His His
145                 150                 155

<210> SEQ ID NO 38
<211> LENGTH: 459
<212> TYPE: DNA
<213> ORGANISM: Artificial Sequence

```
<220> FEATURE:
<223> OTHER INFORMATION: pRphi6-9Rev2TM

<400> SEQUENCE: 38
atgccgtttc cgctggtgaa acaggacccg accagcaaag cgttcaccga agccagcgaa      60
cgctccaccg gcacccagat cctggacgtc gtgaaggccc cgatcggcct gttcggcgac     120
gatgccaaac acgagttcgt gacccgtcag gaacaagcgg tcagcgttgt cagctgggcg     180
gttgcggccg gtctgatctg cgagctgatc ggctaccgtg gtgcgcgctc gggtcgcaaa     240
gcctcgaccc gccaagagca ggccgtttcg gttgtgtcat gggccgtggc agcaggtctg     300
attggtgaac tgattggtta cgcggcgca cgttcgggtc gcaaagcgat cctggccaac      360
attccgtttc tggcgatctc gagcctggtg ccgcgcggct cccgggctgc agctggtacc     420
atggaagctt ctcaccatca ccatcaccat taacttaag                            459

<210> SEQ ID NO 39
<211> LENGTH: 150
<212> TYPE: PRT
<213> ORGANISM: Artificial Sequence
<220> FEATURE:
<223> OTHER INFORMATION: pRphi6-9Rev2TM

<400> SEQUENCE: 39

Met Pro Phe Pro Leu Val Lys Gln Asp Pro Thr Ser Lys Ala Phe Thr
  1               5                  10                  15

Glu Ala Ser Glu Arg Ser Thr Gly Thr Gln Ile Leu Asp Val Val Lys
             20                  25                  30

Ala Pro Ile Gly Leu Phe Gly Asp Asp Ala Lys His Glu Phe Val Thr
         35                  40                  45

Arg Gln Glu Gln Ala Val Ser Val Val Ser Trp Ala Val Ala Ala Gly
     50                  55                  60

Leu Ile Cys Glu Leu Ile Gly Tyr Arg Gly Ala Arg Ser Gly Arg Lys
 65                  70                  75                  80

Ala Ser Thr Arg Gln Glu Gln Ala Val Ser Val Val Ser Trp Ala Val
                 85                  90                  95

Ala Ala Gly Leu Ile Gly Glu Leu Ile Gly Tyr Arg Gly Ala Arg Ser
            100                 105                 110

Gly Arg Lys Ala Ile Leu Ala Asn Ile Pro Phe Leu Ala Ile Ser Ser
        115                 120                 125

Leu Val Pro Arg Gly Ser Arg Ala Ala Ala Gly Thr Met Glu Ala Ser
    130                 135                 140

His His His His His His
145                 150

<210> SEQ ID NO 40
<211> LENGTH: 444
<212> TYPE: DNA
<213> ORGANISM: Artificial Sequence
<220> FEATURE:
<223> OTHER INFORMATION: pRphi6-9Rev3TM

<400> SEQUENCE: 40
atgccgtttc cgctggtgaa acaggacccg accagcaaag cgttcaccga agccagcgaa      60
cgctccaccg gcacccagat cctggacgtc gtgaaggccc cgatcggcct gttcggcgac     120
gatgccaaac acgagttcgt gacccgtcag gaacaagcgg tcagcgttgt cagctgggcg     180
gttgcggccg gtctgatctg cgagctgatc ggctaccgtg gtgcgcgctc gacccgccaa     240
gagcaggccg tttcggttgt gtcatgggcc gtggcagcag gtctgattgg tgaactgatt     300
```

```
ggttatcgcg gcgcacgttc gggtcgcaaa gcgatcctgg ccaacattcc gtttctggcg    360
atctcgagcc tggtgccgcg cggctcccgg gctgcagctg gtaccatgga agcttctcac    420
catcaccatc accattaact taag                                           444
```

<210> SEQ ID NO 41
<211> LENGTH: 145
<212> TYPE: PRT
<213> ORGANISM: Artificial Sequence
<220> FEATURE:
<223> OTHER INFORMATION: pRphi6-9Rev3TM

<400> SEQUENCE: 41

```
Met Pro Phe Pro Leu Val Lys Gln Asp Pro Thr Ser Lys Ala Phe Thr
 1               5                  10                  15

Glu Ala Ser Glu Arg Ser Thr Gly Thr Gln Ile Leu Asp Val Val Lys
            20                  25                  30

Ala Pro Ile Gly Leu Phe Gly Asp Asp Ala Lys His Glu Phe Val Thr
        35                  40                  45

Arg Gln Glu Gln Ala Val Ser Val Val Ser Trp Ala Val Ala Ala Gly
    50                  55                  60

Leu Ile Cys Glu Leu Ile Gly Tyr Arg Gly Ala Arg Ser Thr Arg Gln
65                  70                  75                  80

Glu Gln Ala Val Ser Val Val Ser Trp Ala Val Ala Ala Gly Leu Ile
                85                  90                  95

Gly Glu Leu Ile Gly Tyr Arg Gly Ala Arg Ser Gly Arg Lys Ala Ile
            100                 105                 110

Leu Ala Asn Ile Pro Phe Leu Ala Ile Ser Ser Leu Val Pro Arg Gly
        115                 120                 125

Ser Arg Ala Ala Ala Gly Thr Met Glu Ala Ser His His His His His
    130                 135                 140

His
145
```

<210> SEQ ID NO 42
<211> LENGTH: 28
<212> TYPE: DNA
<213> ORGANISM: Artificial Sequence
<220> FEATURE:
<223> OTHER INFORMATION: forward primer for P2X

<400> SEQUENCE: 42

```
gagatatctg gcgggctgct gcgccgcg                                        28
```

<210> SEQ ID NO 43
<211> LENGTH: 30
<212> TYPE: DNA
<213> ORGANISM: Artificial Sequence
<220> FEATURE:
<223> OTHER INFORMATION: reverse primer for P2X

<400> SEQUENCE: 43

```
ggaagcttcc tggtccagct cactagcaag                                      30
```